United States Patent
Saito

(10) Patent No.: US 10,251,538 B2
(45) Date of Patent: Apr. 9, 2019

(54) ENDOSCOPE SYSTEM AND METHOD FOR CONTROLLING THE SAME

(75) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1730 days.

(21) Appl. No.: 13/538,682

(22) Filed: Jun. 29, 2012

(65) Prior Publication Data

US 2013/0030268 A1  Jan. 31, 2013

(30) Foreign Application Priority Data

Jul. 25, 2011  (JP) .................................. 2011-161647

(51) Int. Cl.
| | |
|---|---|
| *A61B 1/00* | (2006.01) |
| *A61B 1/04* | (2006.01) |
| *A61B 1/05* | (2006.01) |
| *A61B 1/06* | (2006.01) |
| *A61B 1/07* | (2006.01) |

(Continued)

(52) U.S. Cl.
CPC .......... *A61B 1/043* (2013.01); *A61B 1/00009* (2013.01); *A61B 1/05* (2013.01); *A61B 1/063* (2013.01); *A61B 1/0638* (2013.01); *A61B 1/0653* (2013.01); *A61B 1/07* (2013.01); *A61B 1/313* (2013.01); *A61B 5/1032* (2013.01)

(58) Field of Classification Search
USPC .................................................. 600/325, 339
See application file for complete search history.

(56) References Cited

U.S. PATENT DOCUMENTS

| | | | | | |
|---|---|---|---|---|---|
| 4,998,973 | A | * | 3/1991 | Kikuchi ........................ | 600/109 |
| 5,512,940 | A | * | 4/1996 | Takasugi et al. ............... | 348/71 |
| 7,236,813 | B2 | * | 6/2007 | Parker .......................... | 600/323 |

(Continued)

FOREIGN PATENT DOCUMENTS

| | | |
|---|---|---|
| JP | 63-311937 A | 12/1988 |
| JP | 6-315477 A | 11/1994 |

(Continued)

OTHER PUBLICATIONS

Chen et al. Estimation of regional hemoglobin concentration in biological tissues using diffuse reflectance spectroscopy with a novel spectral interpretation algorithm. 2011 Phys.Med.Biol. 56:3985-4000.*

(Continued)

*Primary Examiner* — Tse W Chen
*Assistant Examiner* — Patrick M Mehl
(74) *Attorney, Agent, or Firm* — Birch, Stewart, Kolasch & Birch, LLP

(57) ABSTRACT

In a blood information acquisition mode for obtaining an oxygen saturation level of hemoglobin in a blood vessel, preliminary imaging and main imaging are performed. In the preliminary imaging, a normal internal body part is imaged. A blood information calculation section calculates an oxygen saturation level of each pixel. A changing section corrects standard reference data in accordance with a difference between an average of the oxygen saturation levels obtained in the preliminary imaging and a predetermined standard value of the oxygen saturation level. In the subsequent main imaging, corrected reference data is used to calculate an oxygen saturation level of each pixel corresponding to an internal body part being observed.

21 Claims, 13 Drawing Sheets

(51) Int. Cl.
*A61B 1/313* (2006.01)
*A61B 5/103* (2006.01)

(56) References Cited

U.S. PATENT DOCUMENTS

| | | | | |
|---|---|---|---|---|
| 2004/0024296 | A1* | 2/2004 | Krotkov et al. | 600/322 |
| 2006/0173266 | A1* | 8/2006 | Pawluczyk et al. | 600/407 |
| 2008/0294105 | A1 | 11/2008 | Gono et al. | |
| 2008/0306366 | A1 | 12/2008 | Ohki et al. | |
| 2009/0147999 | A1* | 6/2009 | Maeda et al. | 382/106 |
| 2010/0063355 | A1* | 3/2010 | Matsuura | 600/109 |

FOREIGN PATENT DOCUMENTS

| | | | |
|---|---|---|---|
| JP | 2000-271105 A | | 10/2000 |
| JP | 2011-92690 A | | 5/2011 |
| WO | WO 2006025940 A2 | * | 3/2006 |

OTHER PUBLICATIONS

Fang et al. Time-domain laser-induced fluorescence spectroscopy apparatus for clinical diagnostics. 2004 Rev.Scient.Inst. 75:151-162.*

Fawzy. Quantification of mucosa oxygenation using three discrete spectral bands of visible light. 2009 J.Biophoton. 2:744-749.*

Friedland et al. Measurement of mucosal capillary hemoglobin oxygen saturation in the colon by reflectance spectrophotometry. 2003 Gastrointestinal Endoscopy 57:492-497.*

Prahl. Tabulated molar extinction coefficient for hemoglobin in water 1998 http://omlc.org/spectra/hemoglobin/summary.html 7 pages.*

Schmitt et al. New methds for whole blood oxymetry. 1986 Ann. Biomed.Engin. 14:35-52.*

Sharma et al. The utility of a novel narrow band imaging endoscopy system in patients with Barrett s esophagus. 2006 Gastrointestinal Endoscopy 64;167-175.*

Chinese Office Action and English translation thereof dated Mar. 31, 2015 for Application No. 20121226039.6.

European Search Report dated Nov. 13, 2012 issued in European Patent Application No. 12174084.9.

Japanese Office Action and English translation thereof dated Jan. 14, 2015 for Application No. 2013-244819.

Chinese Office Action and English translation thereof dated Nov. 26, 2015 for Application No. 201210226039.6.

European Communication Pursuant to Article 94(3) EPC dated Dec. 8, 2017, for corresponding European Application No. 12174084.9.

* cited by examiner

ENDOSCOPE SYSTEM AND METHOD FOR CONTROLLING THE SAME

BACKGROUND OF THE INVENTION

1. Field of the Invention

The present invention relates to an endoscope system for obtaining information of an oxygen saturation level of hemoglobin in blood in a blood vessel of living tissue and a method for controlling the same.

2. Description Related to the Prior Art

Examinations and acquisition of biological information, for example, blood information, using endoscopes have been common in the medical field. As is well known, the endoscope is provided with an insert section to be inserted into a body cavity of a subject. Illumination light is applied from a distal portion of the insert section to an internal body part in the body cavity. An image sensor disposed in the distal portion captures an image of the internal body part.

Conventionally, a white light source such as a xenon lamp or a metal halide lamp is used as a light source of the endoscope. Recently, a method for imaging the internal body part illuminated with narrowband light (special light) has gathered attention. This method facilitates finding a lesion (see U.S. Patent Application Publication No. 2008/0294105 corresponding to Japanese Patent No. 3583731).

A method for obtaining blood information, for example, an oxygen saturation level of hemoglobin in blood in a blood vessel, based on an image signal has been researched. The image signal is obtained while the internal body part is illuminated with the narrowband light. For example, in Japanese Patent Laid-Open Publication No. 06-315477, two or more wavelength sets of narrowband light in wavelength bands of 300 to 400 nm, around 400 nm, 400 to 500 nm, 500 to 600 nm, and 450 to 850 nm, are used. Each wavelength set includes a wavelength at which absorbance varies with the oxygen saturation level of hemoglobin and a wavelength at which the absorbance is substantially unaffected by the oxygen saturation level.

In the method disclosed in the Japanese Patent Laid-Open Publication No. 06-315477, a function having a parameter, for example, a ratio between two color pixel values, or a data table is provided as reference data in advance. The information of the oxygen saturation level is obtained from the reference data.

The reference data is based on data of typical living tissue. Actually, however, the reference data varies depending on a characteristic of an internal body part to be observed, for example, structure, thickness, and vascular density of a mucosal layer. The characteristic of the internal body part varies depending on an individual difference or a digestive organ on which the internal body part is located. Accordingly, when the oxygen saturation level of the living tissue with an atypical characteristic is calculated using the typical reference data, reliability of the calculation decreases.

The Japanese Patent Laid-Open Publication No. 06-315477 does not disclose such decrease in reliability of the calculation of the oxygen saturation level and a solution to it.

SUMMARY OF THE INVENTION

An object of the present invention is to provide an endoscope system and a method for controlling the same for obtaining information of an oxygen saturation level with high reliability.

To achieve the above and other objects, an endoscope system of the present invention includes a lighting section, an image sensor, a storage section, a changing section, and a calculation section. The lighting section applies measurement light to an internal body part of a subject. The image sensor images the internal body part illuminated with the measurement light to output a color pixel value of each pixel. The storage section stores standard reference data that defines a correlation between the color pixel value and an oxygen saturation level. The changing section changes the standard reference data to corrected reference data in accordance with a characteristic of the internal body part. The calculation section calculates an oxygen saturation level of the internal body part from the each color pixel value based on the corrected reference data.

It is preferable that the endoscope system further includes a control section for executing preliminary imaging for changing the standard reference data and main imaging for obtaining the oxygen saturation level of the internal body part using the corrected reference data. In the preliminary imaging, it is preferable that the image sensor images a normal internal body part with no lesion while the normal internal body part is illuminated with the measurement light. It is preferable that the calculation section calculates a pre-oxygen saturation level of the normal internal body part based on the standard reference data and a pre-color pixel value obtained from the image sensor during the preliminary imaging. It is preferable that the changing section changes the standard reference data to the corrected reference data in accordance with a difference between the pre-oxygen saturation level and a predetermined standard value of the oxygen saturation level.

It is preferable that the pre-oxygen saturation level is an average of the oxygen saturation levels of a whole or a part of the internal body part.

It is preferable that the control section selectively executes a normal observation mode in which the image sensor images a color image substantially same as an image observed with a naked eye while the internal body part is illuminated with white light, and a blood information acquisition mode for performing the main imaging.

It is preferable that the control section executes the preliminary imaging before the main imaging in the blood information acquisition mode.

It is preferable that the color pixel value is composed of three primary color pixel values, and the standard reference data is represented by two or more standard oxygen saturation curves with different oxygen saturation levels in a Cartesian coordinates having two types of ratios as coordinate axes, and the each ratio using two out of the three primary color pixel values. It is preferable that the corrected reference data is composed of two or more corrected oxygen saturation curves that are shifted from the respective standard oxygen saturation curves in accordance with the difference.

It is preferable that the three primary color pixel values are blue, green, and red pixel values. It is preferable that the measurement light is composed of narrowband light and white light, and the lighting section applies the narrowband light and the white light alternately in each of the preliminary imaging and the main imaging. The image sensor obtains a first color image during application of the white light and a second color image during application of the narrowband light. It is preferable that one of the coordinate axis of the Cartesian coordinates is a ratio between a green pixel value and a red pixel value in the first color image and the other coordinate axis is a ratio between the green pixel value in the first color image and a blue pixel value in the second color image. It is preferable that the calculation section uses color pixel values of an image set, being the first color image and the second color image obtained successively. It is preferable that the pre-oxygen saturation level of the normal internal body part is calculated based on the standard oxygen saturation curves on the Cartesian coordinates in the preliminary imaging, and the oxygen saturation level of the internal body part is calculated based on the corrected oxygen saturation curves in the main imaging.

It is preferable that the narrowband light is in a wavelength range in which there is a difference in absorption coefficient between oxyhemoglobin and deoxyhemoglobin.

It is preferable that the lighting section applies each of the narrowband light and the white light for two or more times in the preliminary imaging. It is preferable that the calculation section calculates the oxygen saturation level per image set in the preliminary imaging. It is preferable that the changing section obtains an average of the oxygen saturation levels and uses the average as the pre-oxygen saturation level.

It is preferable that the endoscope system further includes a blood volume calculation section for calculating a blood volume from the ratio between the green pixel value and the red pixel value in the first color image.

It is preferable that the standard value of the oxygen saturation level is determined for each anatomical body part, and the changing section selects the standard value corresponding to the anatomical body part.

It is preferable that the endoscope system further includes an operation input section for inputting a specific anatomical body part.

It is preferable that the endoscope system further includes a location detection section for detecting the anatomical body part based on at least one of the first and second color images. It is preferable that the location detection section detects the anatomical body part based on a blood volume.

It is preferable that the endoscope system further includes an area selection section for selecting a measurement area used for calculation of the average of the pre-oxygen saturation levels of the normal internal body part in the preliminary imaging. It is preferable that the area selection section determines an area in the first color image, from which an extremely bright and extremely dark areas are excluded, as the measurement area. The area selection section may determine an area, with a blood volume greater than a threshold value, as the measurement area. The area selection section may determine an area, with density of blood vessels less than a threshold value, as the measurement area.

It is preferable that the endoscope system further include a display section and a judging section. The displaying section displays a message that advises performing the preliminary imaging such that the normal internal body part is placed in a whole view field of the image sensor. The judging section judges whether the pre-oxygen saturation level is within a permissible range. When the pre-oxygen saturation level is out of the permissible range, it is preferable that the message that advises performing the preliminary imaging is displayed again on the display section.

An endoscope system includes a lighting section, an image sensor, a storage section, a changing section, and a calculation section. The lighting section applies blue narrowband light and white light alternately, or blue narrowband light, red light, and green light sequentially to an internal body part of a subject. The image sensor outputs a blue pixel value of each pixel which imaged the internal body part illuminated with the blue narrowband light, a red pixel value of each pixel which imaged the internal body part illuminated with a red component of the white light or the red light, and a green pixel value of each pixel which imaged the internal body part illuminated with a green component of the white light or the green light. The storage section stores first standard reference data for determining the oxygen saturation level using a ratio between the green pixel value and the red pixel value and a ratio between the green pixel value and the blue pixel value and second standard reference data for defining the blood volume using a ratio between the green pixel value and the red pixel value. The changing section changes the first standard reference data to first corrected reference data. The calculation section calculates the oxygen saturation level of the internal body part based on the first corrected reference data and the blood volume based on the second standard reference data.

It is preferable that the endoscope system further includes a control section for executing preliminary imaging for changing the first standard reference data and main imaging for obtaining the oxygen saturation level and the blood volume of the internal body part using the first corrected reference data and the second standard reference data. In the preliminary imaging, it is preferable that the image sensor images a normal internal body part with no lesion. It is preferable that the calculation section uses a blue, green, and red pixel values obtained by the image sensor in the preliminary imaging to calculate a pre-oxygen saturation level of the normal internal body part from the first standard reference data. It is preferable that the changing section changes the first standard reference data to the first corrected reference data in accordance with a difference between the pre-oxygen saturation level and a predetermined standard value of the oxygen saturation level.

It is preferable that the blue narrowband light has a wavelength range of 470 nm±10 nm.

A method for controlling an endoscope system includes an applying step, an imaging step, a pre-oxygen saturation calculating step, a changing step, and an oxygen saturation calculating step. In the applying step, in preliminary imaging, measurement light is applied to a normal internal body part with no lesion from a distal end of the insert section inserted into a body cavity. In the imaging step, the normal internal body part is imaged with an image sensor provided in the distal end of the insert section during application of the measurement light to obtain a color pixel value of each pixel. In a pre-oxygen saturation calculating step, a pre-oxygen saturation level is calculated from each color pixel value with a calculation section using standard reference data stored in a storage section. In a changing step, the standard reference data in the storage section is changed to corrected reference data in accordance with a difference between an average of the pre-oxygen saturation levels and a predetermined standard value of the oxygen saturation level. In an oxygen saturation level calculating step, in main imaging, an oxygen saturation level is calculated from the each color pixel value of the color pixel that imaged the internal body part, with the use of the corrected reference data.

In the present invention, the standard reference data is changed in accordance with the characteristic of the internal body part. Accordingly, the oxygen saturation level is obtained with high reliability.

In the preliminary imaging, a pre-oxygen saturation level is obtained using the color pixel value and the standard reference data. The standard reference data is changed to the corrected reference data in accordance with the difference between the pre-oxygen saturation level and the standard value. Thereby, the corrected reference data is obtained easily.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
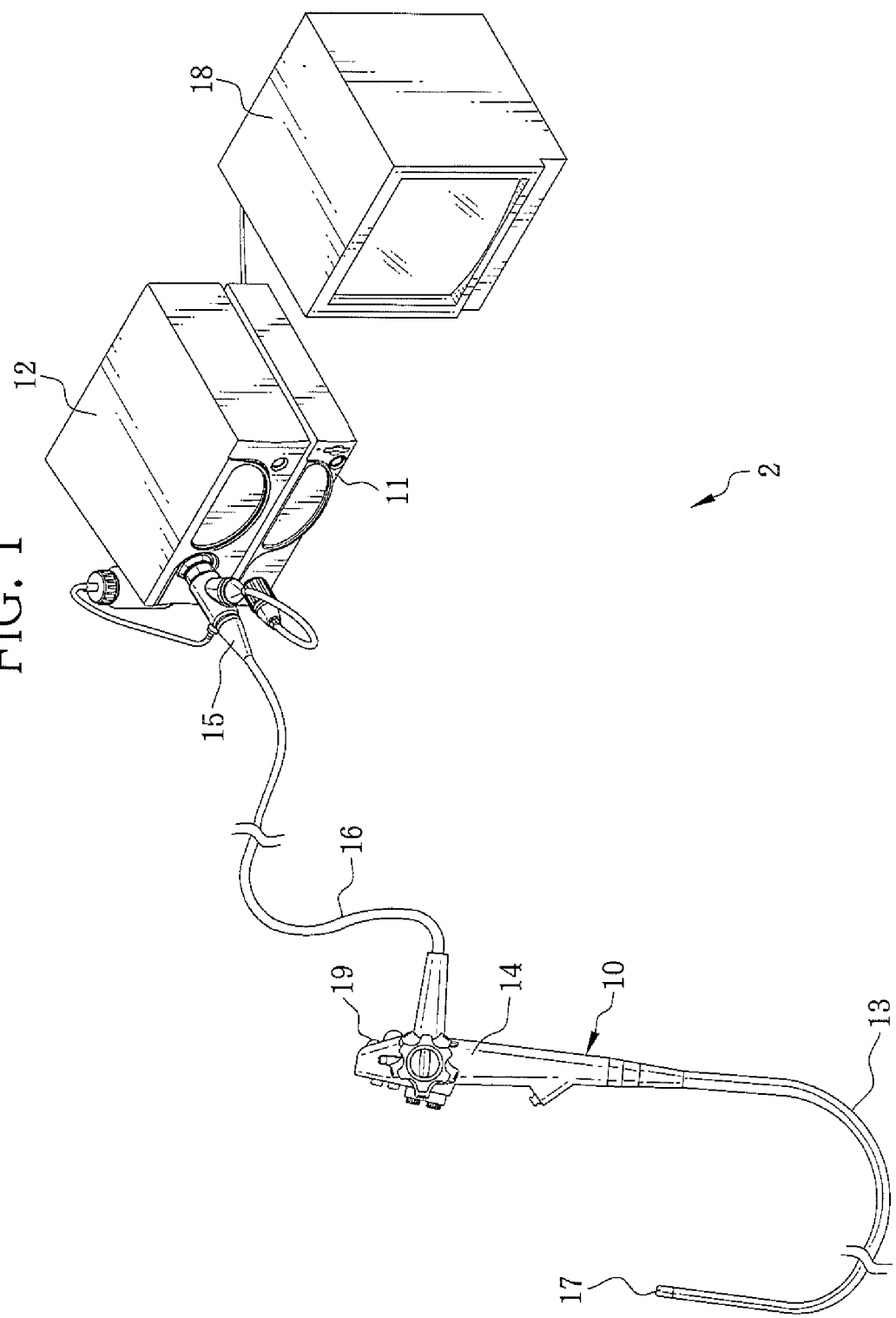
FIG. 1 is an external view of an electronic endoscope system.

In FIG. 1, an electronic endoscope system 2 is composed of an electronic endoscope 10, a processor device 11, and a lighting device 12. The electronic endoscope 10 has, as is well known, a flexible insert section 13 to be inserted into a subject (patient), a handling section 14 joined to a basal portion of the insert section 13, a connector 15 connected to each of the processor device 11 and the lighting device 12, and a universal cord 16 connecting the handling section 14 to the connector 15.

The handling section 14 is provided with operation members, for example, an angle knob for steering a distal portion 17 of the insert section 13 in horizontal and vertical directions, an air/water button for ejecting air and/or water from an air/water nozzle, and a release button for capturing a still observation image.

A forceps inlet is provided on a distal side of the handling section 14. A medical instrument such as an electric scalpel is inserted into the forceps inlet. The forceps inlet is connected to a forceps outlet 40 (see FIG. 3) provided on the distal portion 17 through a forceps channel in the insert section 13.

The processor device 11 is connected electrically to the lighting device 12 and controls operation of the whole electronic endoscope system 2. The processor device 11 supplies power to the electronic endoscope 10 through a transmission cable routed through the universal cord 16 and the insert section 13. The processor device 11 controls operation of a CCD 33 (see FIG. 2) in the distal portion 17. The processor device 11 receives an image signal outputted from the CCD 33 through the transmission cable. The processor device 11 performs various image processing steps to the image signal to produce image data. The image data is sent to a monitor 18, cable-connected to the processor device 11, and displayed as a color observation image.

The electronic endoscope system 2 is provided with a normal observation mode and a blood information acquisition mode (or vascular information acquisition mode). In the normal observation mode, an internal body part of the subject is observed under illumination with white light. In the blood information acquisition mode, the white light and narrowband light is applied to the internal body part to calculate an oxygen saturation level of hemoglobin in blood in a blood vessel of living tissue and a blood volume. A mode selection switch 19 on the handling section 14 is used for switching between the modes. When turned on, the electronic endoscope system 2 is automatically set to the normal observation mode by a command from the processor device 11.

Figure 2:
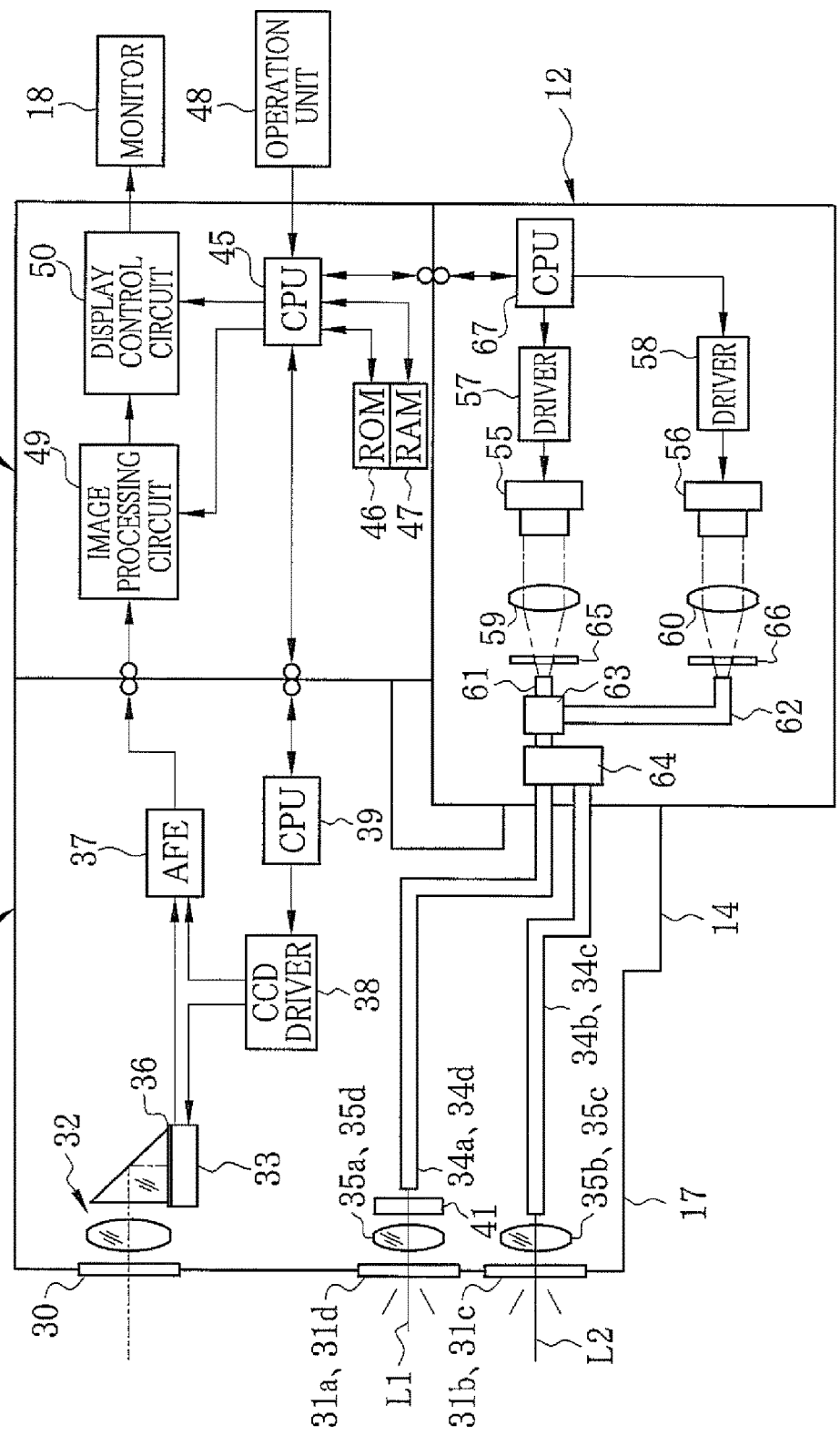
FIG. 2 is a schematic block diagram of the electronic endoscope system.
Figure 3:
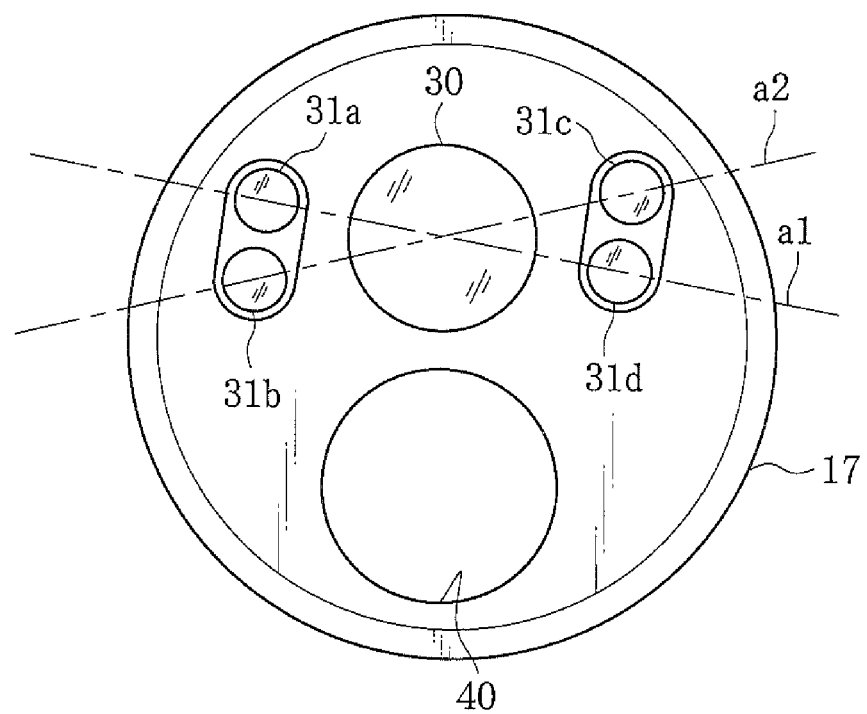
FIG. 3 is a plan view of an end surface of an insert section.

In FIGS. 2 and 3, an imaging window 30 and lighting windows 31a, 31b, 31c, and 31d are provided on an end surface of the distal portion 17 of the insert section 13. The lighting windows 31a and 31b are disposed on a side of the imaging window 30 while the lighting windows 31c and 31d are disposed on the opposite side thereof. Behind the imaging window 30, an objective optical system 32 composed of a lens group and a prism is disposed. The CCD 33 is disposed behind the objective optical system 32.

The lighting windows 31a to 31d apply the illumination light from the lighting device 12 to the internal body part. To be more specific, the lighting window 31a applies the illumination light through a light guide 34a and a lighting lens 35a. The lighting window 31b applies the illumination light through a light guide 34b and a lighting lens 35b. The lighting window 31c applies the illumination light through a light guide 34c and a lighting lens 35c. The lighting window 31d applies the illumination light through a light guide 34d and a lighting lens 35d. The lighting windows 31a and 31d are for the white light. The lighting windows 31b and 31c are for the narrowband light. The lighting windows 31a to 31d are arranged such that an alternate long and short dashed line "a1" between centers of the lighting windows 31a and 31d and an alternate long and short dashed line "a2" between centers of the lighting windows 31b and 31c cross each other at a center of the imaging window 30. This arrangement prevents unevenness in lighting. Each of the lighting system for the white light and that for the narrowband light has two light paths, namely, in total of four paths. In FIG. 2, for the sake of simplification, one of the light paths of each lighting system is illustrated with the numeral of the other light path.

The distal portion 17 may be provided with one light path for each of the white light and the narrowband light, namely, in total of two paths. In this case, two lighting windows are provided.

Figure 4:
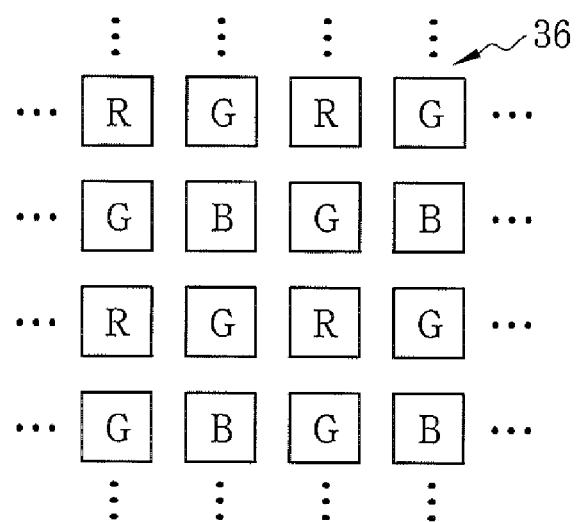
FIG. 4 is an explanatory view of a color filter with a Bayer arrangement.
Figure 5:
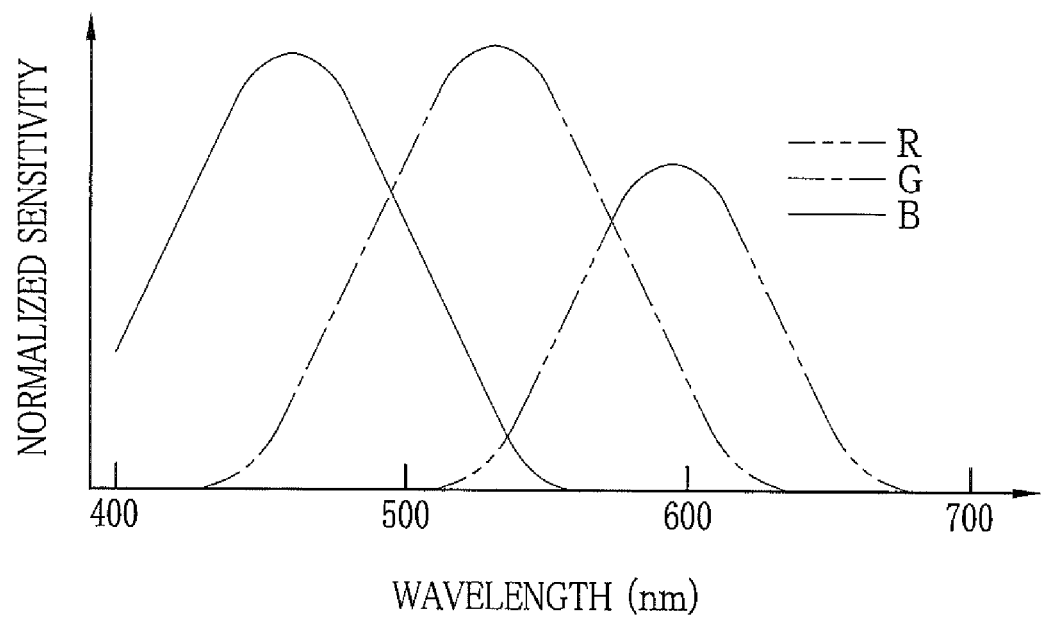
FIG. 5 is a graph showing spectral sensitivity characteristics of each of R, G, and B pixels of a CCD.

Reflection light from the internal body part is incident on the CCD 33 through the imaging window 30 and the objective optical system 32. The CCD 33 converts the reflection light photoelectrically and outputs the image signal in which pixel signals of respective pixels are obtained in time-series. A color filter, e.g. a primary color filter 36, composed of multiple color segments is formed on an imaging surface of the CCD 33. The primary color filter 36 has, for example, a Bayer arrangement (R: red, G: green, and B: blue) as shown in FIG. 4. FIG. 5 shows spectral sensitivity characteristics of each of the R, G, and B pixels of the CCD 33, determined by spectral transmittance of the primary color filter 36 and the spectral sensitivity of the pixels themselves. The R pixel has a sensitivity peak at around 600 nm. The G pixel has a sensitivity peak at around 530 nm. The B pixel has a sensitivity peak at around 460 nm. Wavelength bands of the R, G, and B pixels overlap with each other. For example, both the B and G pixels are sensitive in a wavelength band of 450 nm to 530 nm.

An analog front end (AFE) 37 is composed of a correlated double sampling circuit (CDS), an automatic gain controller (AGC), and an analog/digital converter (A/D), as is well known. The CDS performs correlated double sampling to the image signal outputted from the CCD 33, to remove reset noise and amplification noise occurred in the CCD 33. Then the AGC amplifies the image signal with a gain specified by the processor device 11. Thereafter, the A/D converts the image signal into a digital image signal of a predetermined bit number. The digital image signal is inputted to an image processing circuit 49 of the processor device 11 through a transmission cable.

A CCD driver circuit 38 generates drive pulses (vertical/horizontal scan pulses, electronic shutter pulse, read-out pulse, reset pulse, and the like) for the CCD 33 and a synchronization pulse for the AFE 37. In response to the drive pulse from the CCD driver circuit 38, the CCD 33 carries out imaging operations to output an image signal. Each section of the AFE 37 operates in response to the synchronization pulse from the CCD driver circuit 38.

After the electronic endoscope 10 is connected to the processor device 11, a CPU 39 actuates the CCD driver circuit 38 in response to an operation start command from a CPU 45 of the processor device 11. The CPU 39 adjusts the gain of the AGC in the AFE 37 through the CCD driver circuit 38. The CPU 45 controls the operation of the whole processor device 11. The CPU 45 is connected to each section through a data bus, an address bus, and control lines (all not shown). A ROM 46 stores various programs (OS, application programs, and the like) for controlling the operation of the processor device 11, and data (graphic data, and the like). The CPU 45 reads out the necessary programs and the data from the ROM 46 and loads them into a RAM 47 being a working memory, and runs the programs in sequence. The CPU 45 obtains information, such as text data including examination date and time, a patient's name, and a doctor's name, on an examination-by-examination basis from an operation panel of the processor device 11 or through a network, for example, LAN (local Area Network), and writes the information to the RAM 47.

An operation unit 48 is a well-known input device such as the operation panel provided on a housing of the processor device 11, a mouse, or a keyboard. The CPU 45 operates each section in response to an operation signal from the operation unit 48 or from a release button or the mode selection switch 19 provided on the handling section 14 of the electronic endoscope 10.

The image processing circuit 49 performs various image processing steps such as color interpolation, white balance adjustment, gamma correction, image enhancement, image noise reduction, and color conversion to the image signal inputted from the electronic endoscope 10. The image processing circuit 49 calculates the blood volume and the oxygen saturation level which will be described later.

A display control circuit 50 receives the graphic data from the ROM 46 and examination information (the examination date and time, the patient's name, the doctor's name, or the like) from the RAM 47 through the CPU 45. The graphic data includes a display mask, text data, and a graphical user interface (GUI). The display mask covers an ineffective pixel area of the observation image to display only an effective pixel area. The text data includes the current mode selected. The display control circuit 50 performs various display control processing steps to the image sent from the image processing circuit 49. The display control processing steps include superimposition of the display mask, the text data, and the GUI on the image, and a drawing process for displaying the image on a screen of the monitor 18.

The display control circuit 50 has a frame memory (not shown) for temporarily storing the image from the image processing circuit 49. The display control circuit 50 reads out the image from the frame memory and then converts the image into a video signal (a component signal, a composite signal, or the like) conforming to a display format of the monitor 18. Thereby, an observation image is displayed on the screen of the monitor 18.

In addition, the processor device 11 is provided with a compression circuit, a media I/F, a network I/F, and the like (all not shown). The compression circuit performs image compression with a predetermined compression format (for example, a JPEG format). The media I/F writes the compressed image to a removable medium such as a CF card, a magneto-optical disk (MO), or a CD-R. The network I/F controls transmission of various types of data to and from a network such as the LAN. The compression circuit, the media I/F, the network I/F, and the like are connected to the CPU 45 through the data bus and the like.

Figure 6:
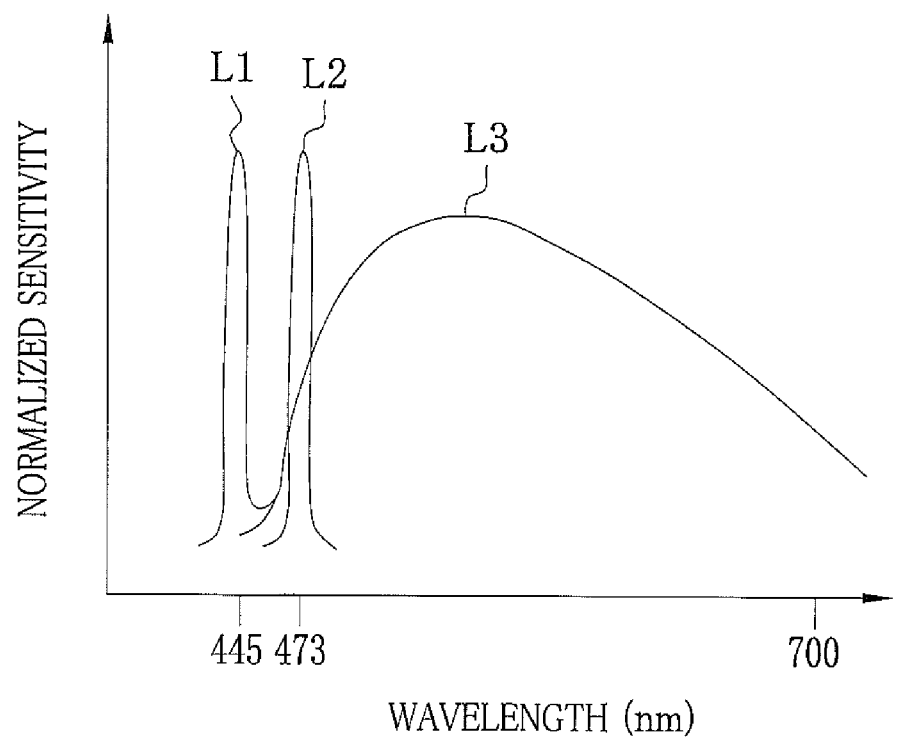
FIG. 6 is a graph showing emission spectra of excitation light, narrowband light, and fluorescence.

The lighting device 12 has a first semiconductor laser 55 and a second semiconductor laser 56. Each of the first and second semiconductor lasers 55 and 56 is broad area type InGaN laser diode, an InGaNAs laser diode, or a GaNAs laser diode. As shown in FIG. 6, the first semiconductor laser 55 emits excitation light for exciting a wavelength changer (phosphor plate) 41 disposed in each of exit ends of the light guides 34*a* and 34*d*, for example, blue excitation light L1 having the center wavelength of 445 nm. The second semiconductor laser 56 emits narrowband light L2 (first measurement light) with a wavelength range of, for example, 470 nm±10 nm, preferably, 473 nm, for measuring the oxygen saturation level of hemoglobin in blood in a blood vessel.

The first and second semiconductor lasers 55 and 56 are driven by light source drivers 57 and 58, respectively. Condenser lenses 59 and 60 gather light from the first and second semiconductor lasers 55 and 56 to allow the light to be incident on light guides 61 and 62, respectively. The light guides 61 and 62 are disposed on exit end sides of the first and second semiconductor lasers 55 and 56, respectively. The light guides 61 and 62 are connected to a combiner 63 being a light mixer. The combiner 63 is connected to a splitter 64 being a light distributor. The light from the light guides 61 and 62 is distributed to four light guides 34a to 34d through the combiner 63 and the splitter 64. A variable aperture stop 65 is disposed between the condenser lens 59 and the light guide 61. A variable aperture stop 66 is disposed between the condenser lens 60 and the light guide 62. The variable aperture stops 65 and 66 control light quantities of the light incident on the light guides 61 and 62, respectively. Instead of using the combiner 63 and the splitter 64, the light from the first and second semiconductor lasers 55 and 56 may be incident directly on light guides 34a to 34d, respectively.

The wavelength changer 41 is disposed between the light guide 34a and the lighting lens 35a. The wavelength changer 41 is also disposed between the light guide 34d and the lighting lens 35d. Each wavelength changer 41 is a glass plate on which several kinds of phosphor are applied or dispersed. The phosphor absorbs a part of the blue excitation light L1 from the first semiconductor laser 55 to emit fluorescence in a wavelength range from green to yellow. The fluorescence (L3 in FIG. 6) from the wavelength changer 41 and the blue excitation light L1 passed through the wavelength changer 41 is mixed to produce the white light. The white light is applied to the internal body part through the lighting windows 31a and 31d. A red wavelength component of the white light is used as second measurement light for measuring the blood volume. A green wavelength component of the white light is used as reference light. Examples of the phosphor include YAG fluorescent substances or $BaMgAl_{10}O_{17}$ (BAM) fluorescent substances. The phosphor sold under the product name Micro White (or MW) (registered trademark) is available.

As shown in FIG. 5, only the B pixel is sensitive to the reflection light (reflected by the internal body part) of the first excitation light L1 with the center wavelength of 445 nm. The B and G pixels are sensitive to the reflection light of the second excitation light L2 with the center wavelength of 473 nm. Because the fluorescence L3 is the light in a broad range of approximately 450 nm to 700 nm, all of the R, G, and B pixels are sensitive to the fluorescence L3.

A CPU 67 of the lighting device 12 communicates with the CPU 45 of the processor device 11. The CPU 67 controls ON/OFF of the first semiconductor laser 55 through the light source driver 57 and that of the second semiconductor laser 56 through the light source driver 58. The CPU 67 also controls light quantity of the first semiconductor laser 55 through the variable aperture stop 65 and that of the second semiconductor laser 56 through the variable aperture stop 66.

One of the normal observation mode and the blood information acquisition mode is selected by using the mode selection switch 19. The CPU (control section) 45 executes the mode selected. When the normal observation mode is selected, the CPU 45 controls the light source driver 57 through the CPU 67 to turn on only the first semiconductor laser 55. Thereby, only the white light, being the mixture of the excitation light L1 at the center wavelength of 445 nm from the first semiconductor laser 55 and the L3 from the wavelength changer 41, is applied as the illumination light to the internal body part.

Figure 7:
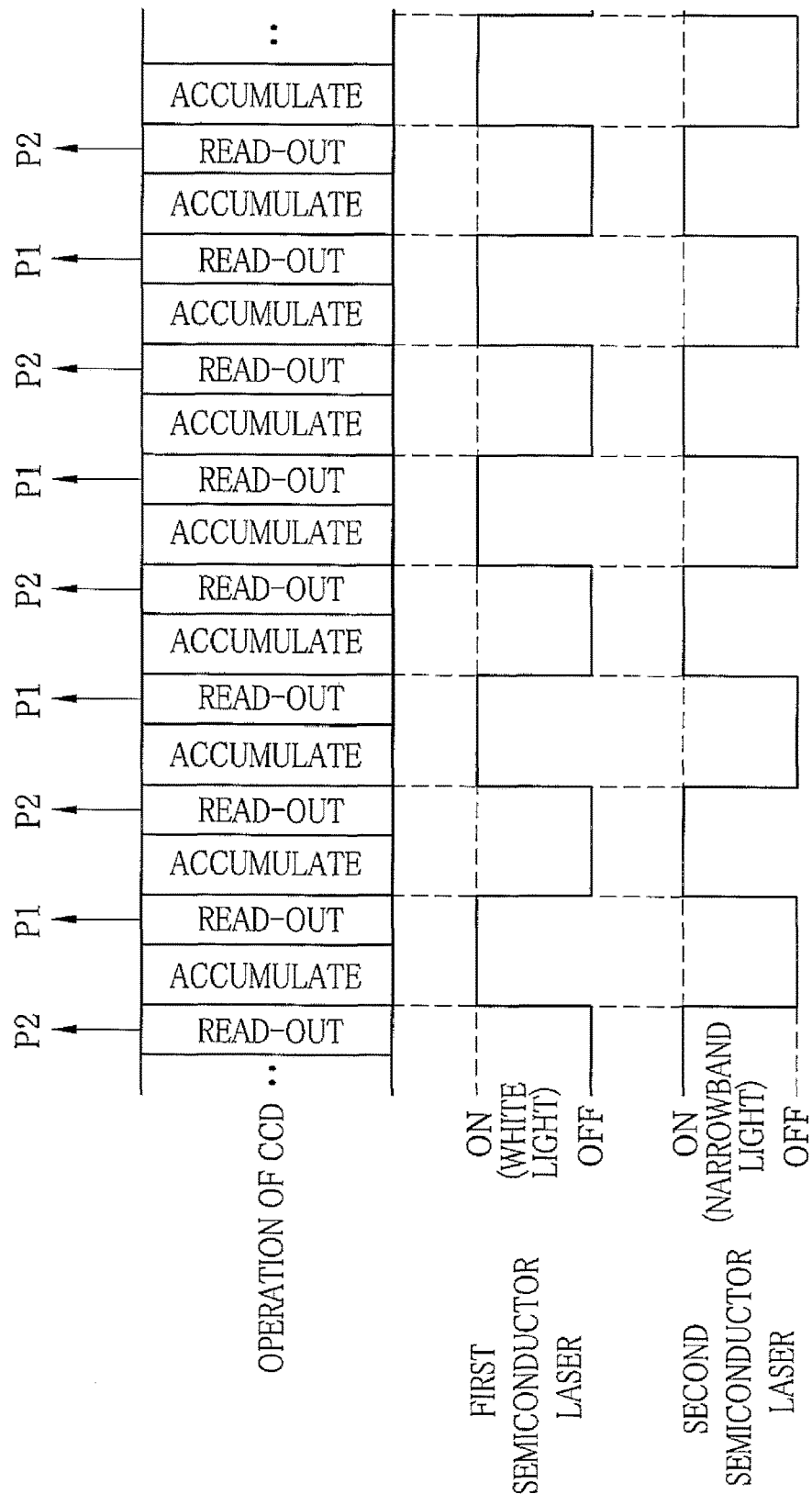
FIG. 7 is a timing chart showing operations of a CCD, and first and second semiconductor lasers.

When the blood information acquisition mode is selected, the CPU 45 controls the light source drivers 57 and 58 through the CPU 67 so as to turn on the lasers 55 and 56 alternately, as shown in FIG. 7, to perform preliminary imaging and main imaging. The lasers 55 and 56 are switched in alternate units, repeatedly. Each unit contains an accumulation period and a read-out period. When the first semiconductor laser 55 is turned on, the white light (L1+L3) is applied to the internal body part. When the second semiconductor laser 56 is turned on, the narrowband light L2 is applied to the internal body part. Note that the lasers 55 and 56 may be turned on only in the accumulation periods of the CCD 33, and turned off in the read-out periods.

Figure 8:
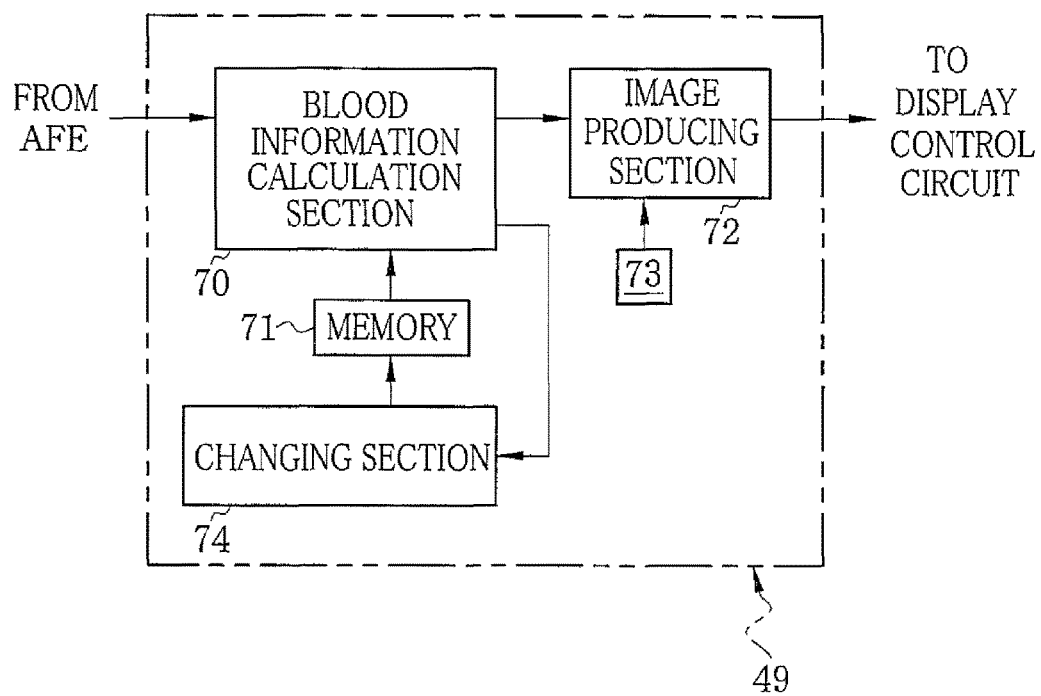
FIG. 8 is a block diagram of an image processing circuit.

In FIG. 8, the image processing circuit 49 is provided with a blood information calculation section (or vascular information calculation section) 70. The blood information calculation section 70 calculates an oxygen saturation level of hemoglobin in blood in a blood vessel and a blood volume in each pixel using an image set, being two consecutive frames of a first color image P1 and a second color image P2 (see FIG. 7) of the internal body part, captured in the blood information acquisition mode. The first color image P1 is captured while the white light (L1+L3) is applied to the internal body part. The second color image P2 is captured while the blue narrowband light L2 is applied to the internal body part. The white light and the blue narrowband light is applied alternately.

The blood information calculation section 70 has a frame memory (not shown) for temporarily storing the image set, being the first and second color images P1 and P2. The blood information calculation section 70 reads out the first and second color images P1 and P2 from the frame memory. The blood information calculation section 70 performs various calculations using color pixel values of the first and second color images P1 and P2, for example, a ratio between the color pixel values of the first and second color images P1 and P2. The color pixel values may not be obtained from the whole of the respective first and second color images P1 and P2. Namely, a ratio of color pixel values between areas of the respective first and second color images P1, and P2, for example, a ratio between a color pixel value of a vascular area of the first color image P1 and a color pixel value of a vascular area of the second color image P2 may be calculated. In this case, the image inputted from the AFE 37 is analyzed before the image is inputted to the blood information calculation section 70. For example, a difference in luminance value between a vascular area and a non-vascular area is referred to, to determine the vascular area in the image. Then, the image and information of the vascular area determined are outputted to the blood information calculation section 70.

The blood information calculation section 70 calculates the oxygen saturation level and the blood volume using the ratio between the color pixel value of the first color image P1 captured under illumination of the white light and the color pixel value of the subsequent second color image P2 captured under illumination of the narrowband light, by way of example. To be more specific, the blood information calculation section 70 calculates a ratio "b2/g1" (a "first ratio" between the B pixel value b2, being a first pixel value, of the second color image P2 and the G pixel value g1, being a third pixel value, of the first color image P1), relative to the corresponding pixels in the first and second color images P1 and P2, and a signal ratio "r1/g1" (a "second ratio" between the R pixel value r1, being a second pixel value, and the G pixel value g1, being the third pixel value, of the first color image P1), and calculates the oxygen saturation level and the blood volume based on reference data in a memory 71 on pixel by pixel basis.

Figure 9:
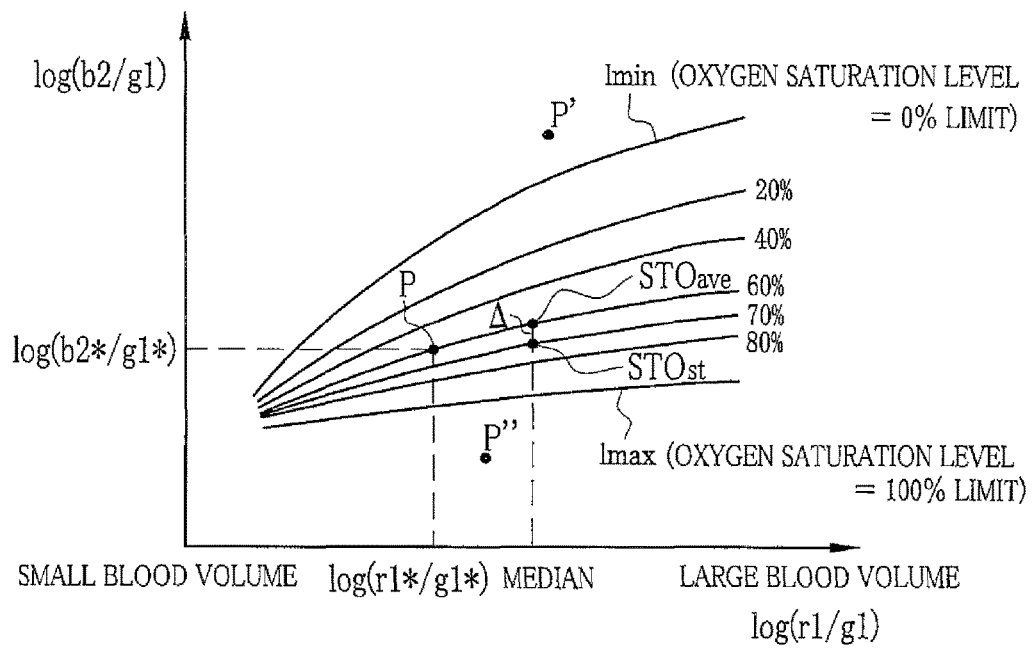
FIG. 9 is a graph of standard reference data by way of example.

The standard reference data related to the oxygen saturation level and the blood volume is stored in the ROM 46, for example. When the power is turned on, the standard reference data is read out from the ROM 46 and written to the memory 71 in the image processing circuit 49. The standard reference data (standard oxygen saturation level information and standard blood volume information) includes a function or a data table that defines a correlation between each signal ratio (between the color pixel values) and the oxygen saturation level or a correlation between a signal ratio and the blood volume. The standard reference data is produced by obtaining the correlation between the each signal ratio and the oxygen saturation level and the correlation between the signal ratio and the blood volume from an experiment or the like. As shown in FIG. 9, the standard oxygen saturation level information is represented by standard oxygen saturation curves with different oxygen saturation levels in Cartesian coordinates or rectangular coordinates having two types of ratios as coordinate axes. The vertical axis is a first signal ratio b2/g1. The horizontal axis is a second signal ratio r1/g1. Gaps between the standard oxygen saturation curves increase in size as the second ratio r1/g1, being the blood volume, increases.

The standard blood volume information is represented by a standard blood volume curve in Cartesian coordinates having the signal ratio r1/g1 as the coordinate axis. Note that in this embodiment, the standard blood volume curve is not changed in accordance with the characteristic of the internal body part. However, the standard blood volume curve may be changed in a manner similar to the oxygen saturation level information.

Figure 10:
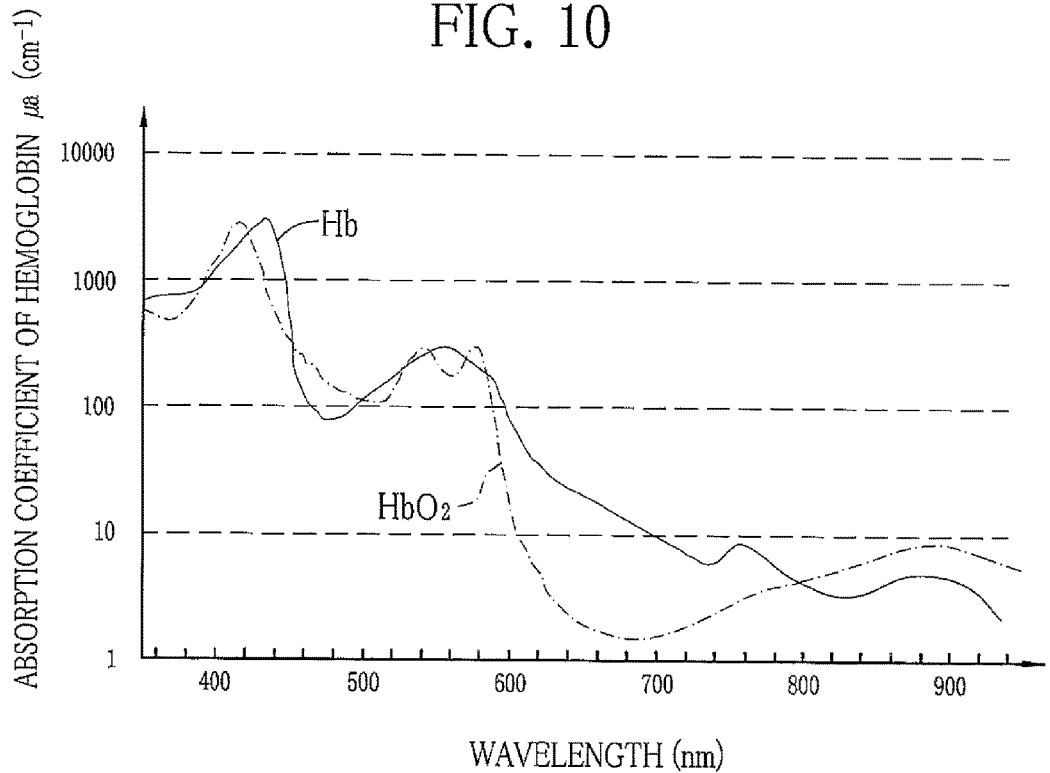
FIG. 10 is a graph showing absorbance of oxyhemoglobin and deoxyhemoglobin.

The correlation between each signal ratio and the oxygen saturation level and the correlation between the signal ratio and the blood volume is closely related to light absorption property and light scattering property of oxyhemoglobin and deoxyhemoglobin shown in FIG. 10. It is easy to obtain information of the oxygen saturation level from a signal acquired under illumination of the light having a wavelength at which a difference between the absorption coefficient of the oxyhemoglobin and the absorption coefficient of the deoxyhemoglobin is large, for example, at 473 nm (that is, in the wavelength band of the narrowband light L2). However, the signal thus acquired is highly dependent on both the oxygen saturation and the blood volume.

Two important points are derived from FIG. 10.

1. In a wavelength range close to 470 nm, for example, in a blue wavelength band with the center wavelength of 470 nm±10 nm, the absorption coefficient varies significantly in accordance with a change in the oxygen saturation.

2. In a red wavelength band from 590 nm to 700 nm, the absorption coefficient appears to vary significantly in accordance with a change in the oxygen saturation. Actually, however, the absorption coefficient is likely to be unaffected by the oxygen saturation because the value of the absorption coefficient is extremely small.

Based on the above-described two points, in the blood information acquisition mode, the blue narrowband light L2 is used as the first measurement light to obtain the B pixel value b2 of the second color image P2 corresponding to the narrowband light L2. The red wavelength component, varying mainly with the blood volume, of the white light is used as the second measurement light to obtain the R pixel value r1 of the first color image P1. Using the first signal ratio b2/g1 dependent on both the oxygen saturation level and the blood volume and the second signal ratio r1/g1 dependent only on the blood volume, the oxygen saturation level of each pixel is calculated accurately without influence of the blood volume.

The blood information calculation section 70 retrieves the oxygen saturation level and the blood volume corresponding to the signal ratios from the data table or inputs the signal ratios into the function. Thus, the oxygen saturation level and the blood volume corresponding to the signal ratios are obtained from the standard reference data or corrected reference data (changed reference data). The blood volume is obtained from the ratio r1*/g1* with the use of the blood volume curve. The oxygen saturation level is represented by the kind (in this example, 60%) of the oxygen saturation curve crossing a point P corresponding to the ratios b2*/g1* and the r1*/g1*. When a point P' corresponding to the ratios b2*/g1* and the r1*/g1* is located above a lower limit line "lmin" (oxygen saturation level=0%), the oxygen saturation level is determined as 0%. When a point P" corresponding to the ratios b2*/g1* and the r1*/g1* is located below an upper limit line "lmax" (oxygen saturation level=100%), the oxygen saturation level is determined as 100%. The oxygen saturation level of the pixel is not calculated when the oxygen saturation level is 0% and 100%.

In the preliminary imaging in the blood information acquisition mode, the blood information calculation section 70 sends a result of the calculation of the oxygen saturation level (pre-oxygen saturation level) to a changing section 74 to produce the corrected reference data (changed reference data). On the other hand, in the main imaging in the blood information acquisition mode, the oxygen saturation level and the blood volume of each pixel calculated in the blood information calculation section 70 is sent to an image producing section 72. The image producing section 72 colors each pixel according to a level of its color pixel value based on a color map to produce the oxygen saturation image and the blood volume image.

Figure 11:
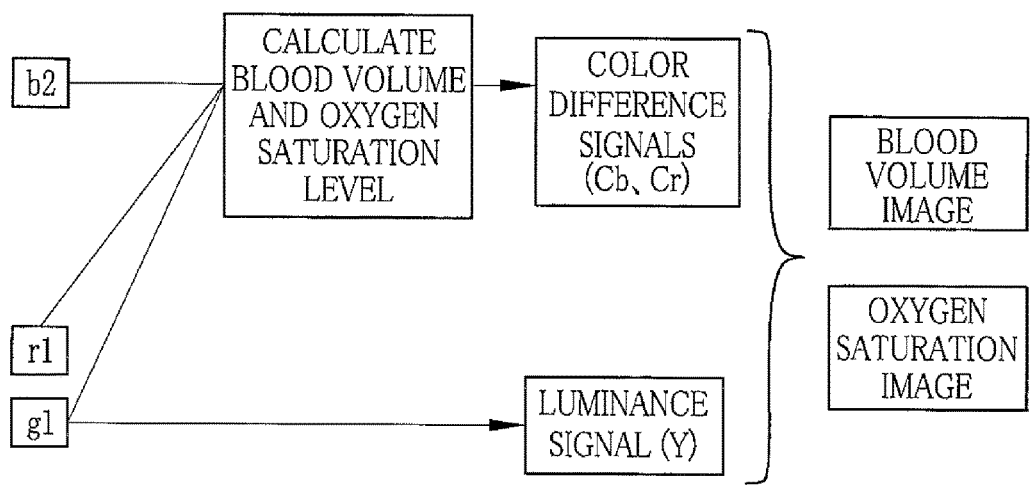
FIG. 11 is a block diagram showing steps for producing a blood volume image and an oxygen saturation image.

As shown in FIG. 11, a video signal sent to the monitor 18 includes a luminance signal Y and color difference signals Cb and Cr. The G pixel value g1 of the first color image P1 is assigned to the luminance signal Y. The blood volume calculated is assigned to the color difference signals Cb and Cr. Thereby, the blood volume image is produced. The G pixel value g1 of the first color image P1 corresponds to the reflection light of the wavelength band in which absorption by hemoglobin is relatively high. Accordingly, the unevenness of mucosa and blood vessels are visually inspected in the image formed based on the G pixel value g1. By assigning the G pixel value g1 to the luminance signal Y, the overall brightness of the blood volume image is determined.

Figure 12A:
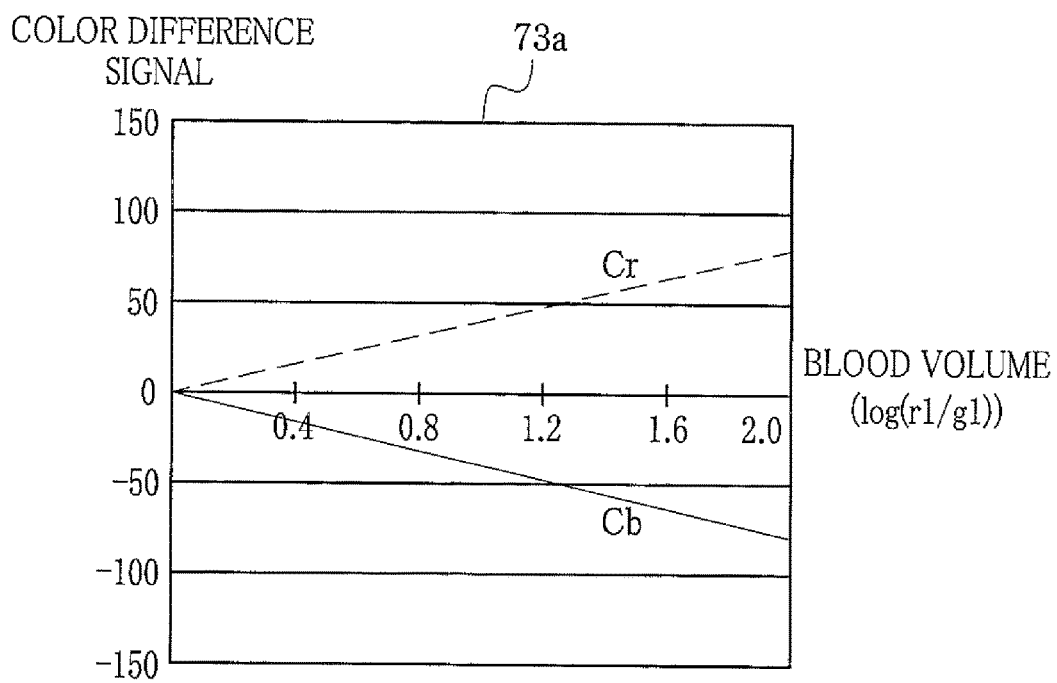
FIG. 12A is a color map for producing the blood volume image.

Based on a color map 73a shown in FIG. 12A, signal values, corresponding to the blood volume, are assigned to the color difference signals Cb and Cr, respectively. In the color map 73a, the signal value of the color difference signal Cb decreases as the blood volume increases. The signal value of the color difference signal Cr, on the other hand, increases as the blood volume increases. Accordingly, the blood volume image increases redness when the blood volume increases. The redness in the blood volume image decreases in chroma when the blood volume decreases and thus the blood volume image becomes monochromatic.

The oxygen saturation image, being a pseudo color image, is produced by assigning the G pixel value g1 to the luminance signal Y and the oxygen saturation level to the color difference signals Cb and Cr in a manner similar to the production of the blood volume image.

Figure 12B:
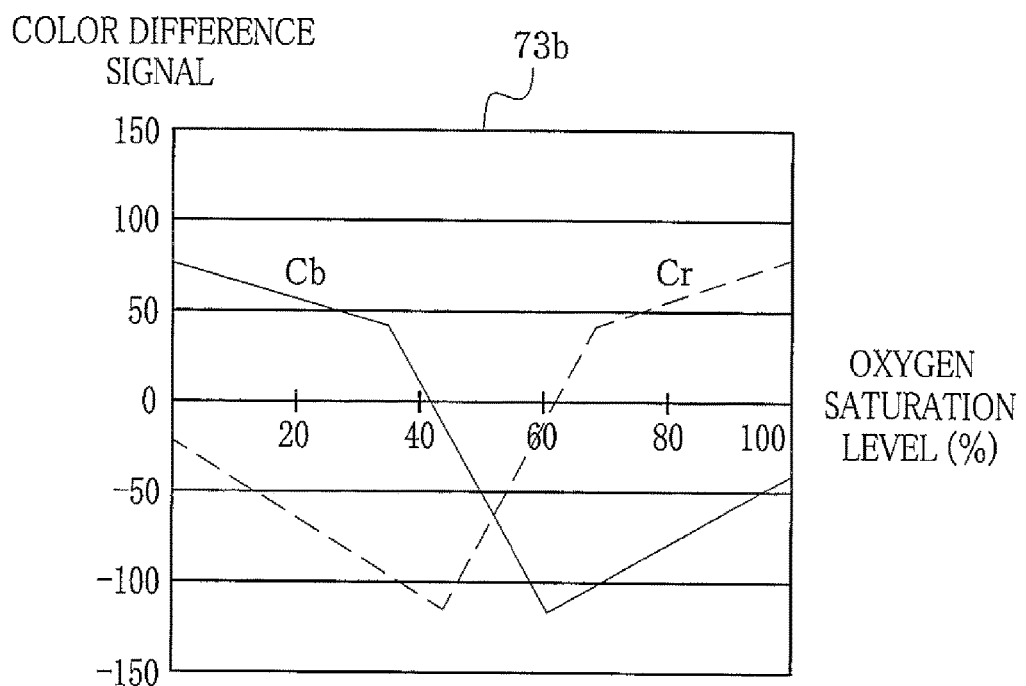
FIG. 12B is a color map for producing the oxygen saturation image.

Based on a color map 73b shown in FIG. 12B, signal values, corresponding to the oxygen saturation level, are assigned to the color difference signals Cb and Cr, respectively. In the color map 73a, when the oxygen saturation level is high, a signal value of the color difference signal Cr is defined positive, while a signal value of the color difference signal Cb is defined negative. When the oxygen saturation level is low, on the contrary, the signal value of the color difference signal Cr is defined negative, while the signal value of the color difference signal Cb is defined positive. When the oxygen saturation level is at a medium level, a relation in magnitude between the signal value of the color difference signal Cr and the signal value of the color difference signal Cb reverses. Accordingly, as the oxygen saturation level increases, the hue or color of the oxygen saturation image changes from blue to light blue to green to yellow to orange to red. Additionally, numerical values of the blood volume and the oxygen saturation level may be superimposed as the text data onto the image produced.

In the normal observation mode, the display control circuit 50 allows the monitor 18 to display a full-color image of the internal body part imaged under illumination of the white light. The full-color image is substantially the same as an image observed with the naked eye. In the main imaging in the blood information acquisition mode, the display control circuit 50 allows the monitor 18 to display one of the blood volume image and the oxygen saturation image, produced in the image producing section 72, singly (single display), or both the blood volume image and the oxygen saturation image side by side (tiled display). The single display and the tiled display are switched manually, or automatically at regular intervals. This facilitates comparison between the images, which improves performance in diagnosing a lesion, for example, undifferentiated early gastric cancer.

Figure 13:
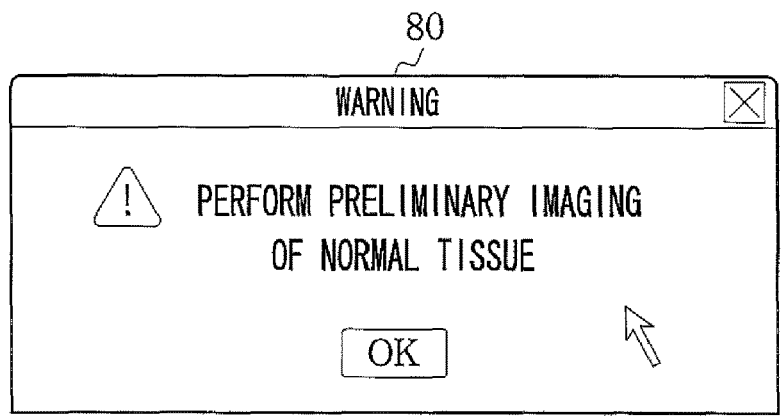
FIG. 13 is an explanatory view showing a message window advising that preliminary imaging needs to be performed.

When the normal observation mode using the white light is switched to the blood information acquisition mode, the CPU 45 allows the monitor 18 to display a message window 80 as shown in FIG. 13. The message window 80 displays a message, for example, "perform preliminary imaging of normal internal body part" advising an operator to position the normal internal body part with no lesion in a whole view field of the electronic endoscope 10 and perform the preliminary imaging to calculate the oxygen saturation level.

When the message window 80 is displayed, the operator observes the image displayed on the monitor 18 and positions the normal internal body part or the internal body part assumed to be normal in the whole view field of the electronic endoscope 10. Then, the operation unit 48 is operated to input the start of the preliminary imaging. Note that the normal internal body part and the internal body part to be observed (the internal body part having a suspected lesion from which the blood volume and the oxygen saturation levels are obtained) are located in the same organ.

When the start of the preliminary imaging is inputted, the CPU 67 switches the illumination light from the successive application of the white light to the alternate applications of the blue narrowband light and the white light. As shown in FIG. 7, the CCD 33 images the normal internal body part illuminated alternately with the white light and the narrowband light. The blood information calculation section 70 uses the standard reference data shown in FIG. 9 to calculate the oxygen saturation level (pre-oxygen saturation level) of each pixel relative to a part or the whole of one image set. The pre-oxygen saturation level calculated is sent to the changing section 74.

The changing section 74 calculates the average of the pre-oxygen saturation levels of the respective pixels in the image set. In the preliminary imaging, two or more image sets are obtained. The average of the pre-oxygen saturation levels of each image set is added and then divided by the total number of the image sets. Thereby, the average "$STO_{ave}$" of the pre-oxygen saturation levels of all the image sets is obtained. Thereafter, a difference $\Delta$ between the average value $STO_{ave}$ and a predetermined standard value "$STO_{st}$" is calculated. The standard value $STO_{st}$ is a typical oxygen saturation level (70%) of normal mucosa of a gastrointestinal tract from the mouth to the anus.

When the difference $\Delta$ between the average value $STO_{ave}$ and the standard value $STO_{st}$ is "0" ($STO_{ave}=STO_{st}$), the changing section 74 does not change or correct the standard reference data.

Figure 14:
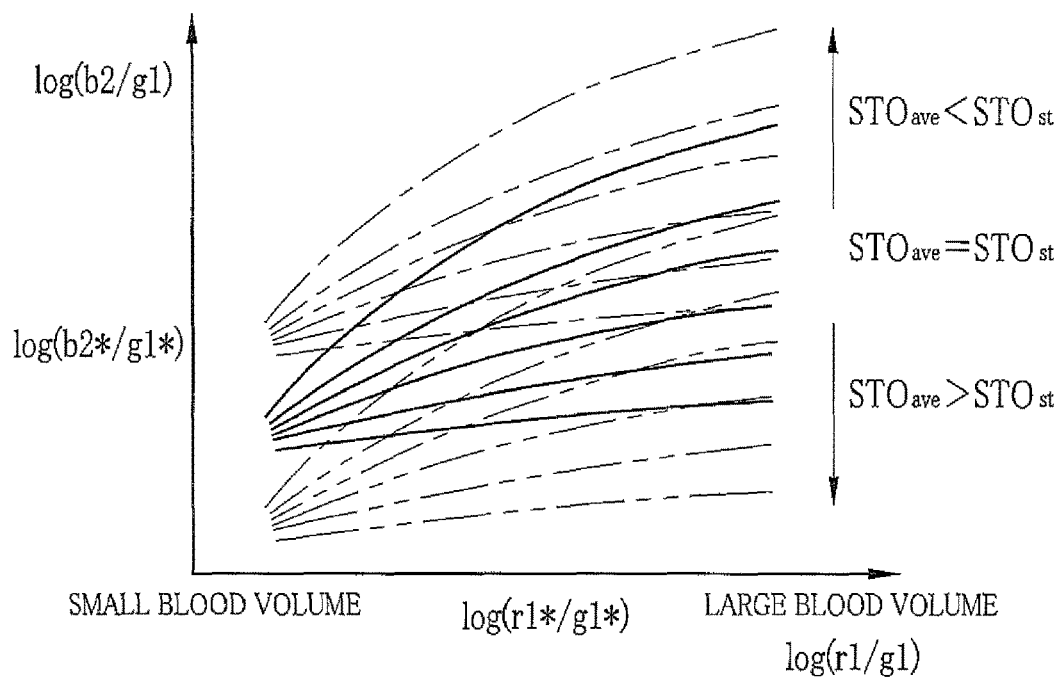
FIG. 14 is an explanatory view of correcting the reference data.

When the difference $\Delta$ between the average value $STO_{ave}$ and the standard value $STO_{st}$ is negative ($STO_{ave}-STO_{st}<0$, namely, $STO_{ave}<STO_{st}$), the standard oxygen saturation curves depicted by solid lines in FIG. 14 are translated vertically upward along the vertical axis as shown in dot and dash lines in FIG. 14 to compensate for the difference and make $STO_{ave}=STO_{st}$. When the difference $\Delta$ between the average value $STO_{ave}$ and the standard value $STO_{st}$ is positive ($STO_{ave}-STO_{st}>0$, namely, $STO_{ave}>STO_{st}$), the standard oxygen saturation curves depicted by the solid lines in FIG. 14 are translated vertically downward along the vertical axis as shown in two dot and dash lines in FIG. 14 to compensate for the difference and make $STO_{ave}=STO_{st}$. Note that when the difference between the average value $STO_{ave}$ and the standard value $STO_{st}$ is "0" ($STO_{ave}=STO_{st}$), the standard oxygen saturation curves are unchanged, namely, the standard oxygen saturation curves shown in FIG. 9 are used.

The amount of the translation is adjusted based on the magnitude of the difference $\Delta$ between the average value $STO_{ave}$ and the standard value $STO_{st}$ with the blood volume fixed to a predetermined value, for example, a median (see FIG. 9). The standard oxygen saturation curves are translated along an axis of the fixed blood volume. The amount of the translation increases as the difference between the average value $STO_{ave}$ and the standard value $STO_{st}$ increases. The changing section 74 stores the corrected oxygen saturation curves in the memory 71 together with the standard oxygen saturation curves. During the preliminary imaging, a blood volume (pre-blood volume) and the average of the pre-blood volumes may be calculated in addition to the pre-oxygen saturation level. The difference $\Delta$ between the average value $STO_{ave}$ and the standard value $STO_{st}$ may be obtained along the line of the average of the pre-blood volumes. The gaps between the standard oxygen saturation curves increase or decrease depending on the blood volume. Accordingly, it is preferable to take the pre-blood volume into consideration in calculating the difference $\Delta$, which offers higher accuracy.

Figure 15:
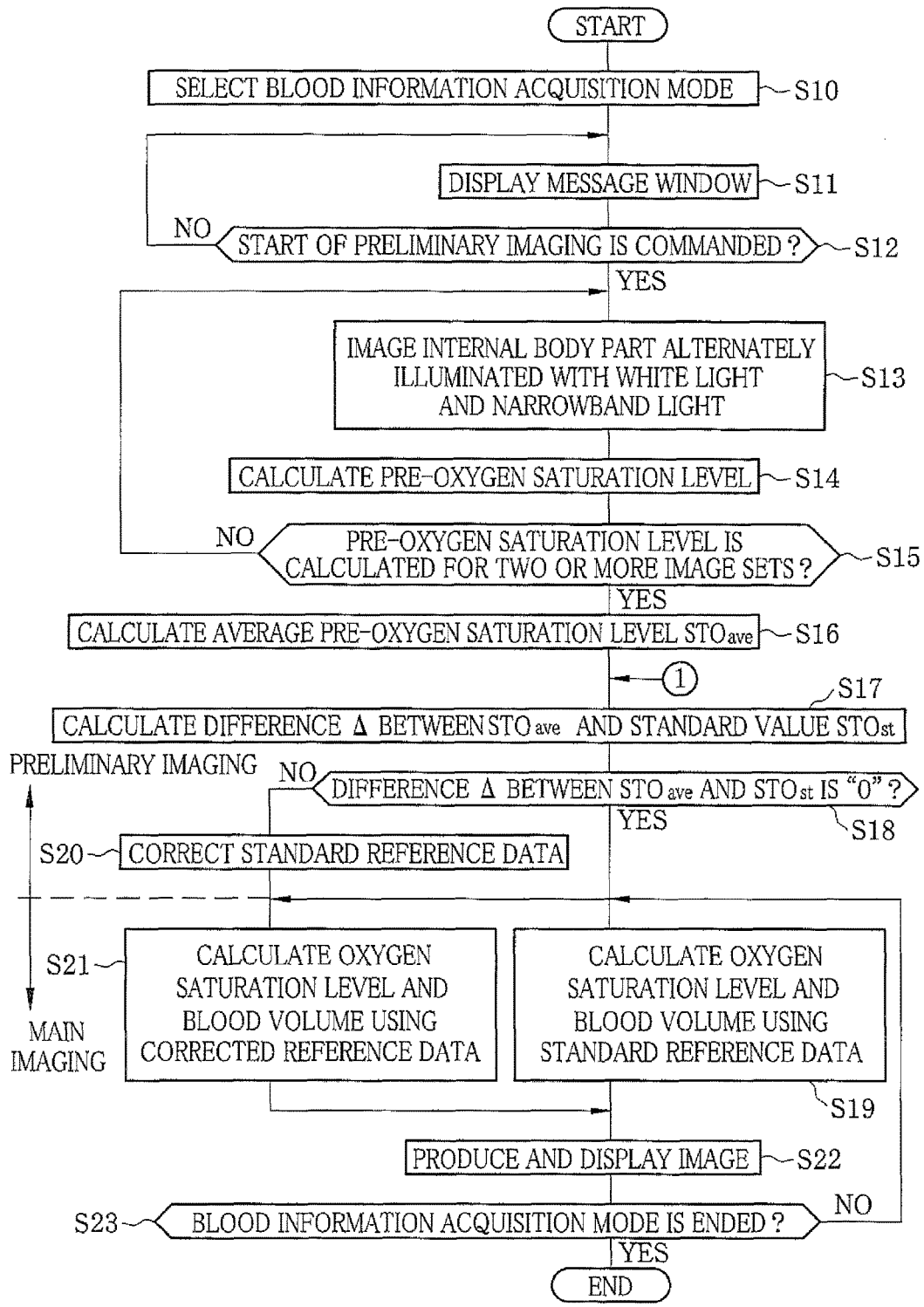
FIG. 15 is a flowchart showing steps in a blood information acquisition mode.

Next, referring to FIG. 15, an operation of the above-configured electronic endoscope system 2 is described. The operator operates the operation unit 48 to input information or the like related to the subject and commands the start of the examination. Then, the operator inserts the insert section 13 of the electronic endoscope 10 into the body cavity. While the lighting device 12 illuminates the body cavity, the operator images the body cavity with the CCD 33.

The image signal outputted from the CCD 33 is subjected to various processes in the respective sections of the AFE 37. Then, the image signal is inputted to the image processing circuit 49. The image processing circuit 49 performs various image processing steps to the image signal to produce an image. The image is inputted to the display control circuit 50. The display control circuit 50 performs various display control processing steps to the image in accordance with the graphic data. Thereby, a full-color observation image is displayed on the monitor 18.

The normal observation mode is selected when the electronic endoscope 10 is inserted into the body cavity. In the normal observation mode, under the command of the CPU 45, the CPU 67 turns on the first semiconductor laser 55.

Thereby, the white light is applied from the lighting windows 31a and 31d. The insert section is inserted while a wide observation view field is ensured by the illumination of the white light. When the electronic endoscope 10 reaches close to the internal body part of interest, the internal body part is observed through a color image on the monitor 18 while the direction and the position of the distal portion 17 of the insert section 13 are adjusted. During the observation, a still image is captured by using the release button or a medical instrument is inserted into the forceps channel of the electric endoscope 10 to remove the lesion or to give medicine to the lesion, for example.

During the normal observation mode, when a lesion requiring detailed observation is found, as illustrated in S10 in FIG. 15, the mode selection switch 19 is used to select the blood information acquisition mode. When the normal observation mode is switched to the blood information acquisition mode, the display control circuit 50 allows the monitor 18 to display the message window 80 that advises the operator to perform the preliminary imaging (S11). A normal internal body part is placed inside the view field of the electronic endoscope 10 and then the start of the preliminary imaging is commanded (YES in S12). Thereby, the CPU 67 controls the lasers 55 and 56 to be turned on alternately in the respective frames ("accumulation and read-out" periods). The CCD 33 captures reflection light of the white light (L1+L3) and that of the narrowband light L2 to output the first color image P1 and the second color image P2 respectively and alternately (S13).

In the image processing circuit 49, the blood information calculation section 70 calculates a ratio between the color pixel value of the first color image P1 and the color pixel value of the second color image P2. The first and second color images P1 and P2 are imaged successively and used as the image set. The pre-oxygen saturation level is calculated using the standard reference data (standard oxygen saturation curves) (S14). The imaging (S13) and the calculation of the pre-oxygen saturation level (S14) are repeated for two or more image sets (NO in S15).

The blood information calculation section 70 outputs the result of the calculation of the pre-oxygen saturation level of each pixel to the changing section 74. The changing section 74 calculates the average value $STO_{ave}$ of the pre-oxygen saturation levels of all the image sets (S16). Then, the difference $\Delta$ between the average value $STO_{ave}$ and the standard value $STO_{st}$ is calculated (S17). When the difference $\Delta$ between the average value $STO_{ave}$ and the standard value $STO_{st}$ is "0" ($STO_{ave}=STO_{st}$) (YES in S18), the changing section 74 does not change or correct the standard reference data (standard oxygen saturation curves), and the oxygen saturation level and the blood volume of each pixel are calculated using the standard reference data (S19). On the other hand, when the difference $\Delta$ between the average value $STO_{ave}$ and the standard value $STO_{st}$ is not "0" ($STO_{ave}<STO_{st}$ or $STO_{ave}>STO_{st}$) (NO in S18), the changing section 74 corrects the standard reference data so as to compensate for the difference $\Delta$ between the average value $STO_{ave}$ and the standard value $STO_{st}$. Thus, the corrected reference data is produced and written to the memory 71 (S20).

When the preliminary imaging is completed, the start of the main imaging is commanded. The main imaging is performed with the distal portion 17 directed toward the internal body part to be observed, for example, a lesion. In the main imaging, the narrowband light and the white light is alternately applied to the internal body part as in the preliminary imaging. The first color image P1 and the second color image P2 are imaged alternately under the respective applications of light. The first and second color images P1 and P2 are used as the image set. The signal ratios r1/g1 and the b2/g1 are calculated relative to each pixel. The oxygen saturation level of each pixel is calculated using the signal ratios and the corrected reference data (corrected oxygen saturation curves) of the oxygen saturation level. The blood volume of each pixel is calculated using the signal ratio r1/g1 and the standard reference data (blood volume curve) of the blood volume (S21).

The oxygen saturation level and the blood volume of each pixel calculated by the blood information calculation section 70 are sent to the image producing section 72, and colored depending on their levels. The oxygen saturation image and the blood volume image expressed in pseudo color are displayed on the monitor 18 side by side (S22). The oxygen saturation image and the blood volume image are updated per image set. The oxygen saturation image and the blood volume image displayed on the monitor 18 are observed to diagnose whether cancer tissue exists in the lesion.

When the detailed observation of the lesion is completed, the mode selection switch 19 is used to end the blood information acquisition mode (YES in S23). In this case, the blood information acquisition mode is switched to the normal observation mode, and the normal observation under the successive application of the white light is started.

In the present invention, the average value $STO_{ave}$ of the pre-oxygen saturation levels of blood in the blood vessel of the normal internal body part is obtained. When the average value $STO_{ave}$ does not coincide with the standard value $STO_{st}$, the standard reference data is corrected to compensate for the difference between the average value $STO_{ave}$ and the standard value $STO_{st}$. Then, the oxygen saturation level is calculated using the corrected reference data. Thereby, accurate information of the oxygen saturation level is constantly obtained with reproducibility without influence of an individual difference between patients. This increases reliability of the diagnosis using the oxygen saturation level, and enables early detection of cancer tissue.

In the above embodiment, the single standard value $STO_{st}$ is used for the comparison. Alternatively, the standard value $STO_{st}$ may be set for each body part of the gastrointestinal tract, for example, esophagus and stomach, and stored. Setting the standard value $STO_{st}$ on a body part by body part basis further improves the reliability of the calculation of the oxygen saturation level. In this case, note that the operator inputs the internal body part (or organ) being observed through the operation unit 48 or the like when commanding the start of the preliminary imaging. In response to an operation input signal, the standard value $STO_{st}$ is switched to the value corresponding to the internal body part inputted. Alternatively, to omit inputting the internal body part, an anatomical location of the body part being observed may be automatically detected. The standard value $STO_{st}$ is switched to a value corresponding to the anatomical location in response to a result of the automatic detection.

To automatically detect the anatomical location of the internal body part, a signal ratio r1/g1 between the R pixel value r1 of the first color image P1 and the G pixel value g1 of the first color image P1, being the index of the blood volume, is compared with a threshold value. For example, the blood volume of the esophagus is relatively low. The blood volume of the stomach is relatively high. The blood volume of the large intestine is between those of the esophagus and the stomach. The changing section 74 compares the ratio r1/g1 sent from the blood information calculation section 70 with the threshold value predetermined for distinguishing the internal body part. Based on the ratio r1/g1 and the result of the comparison, the changing section 74 identifies or determines the internal body part being observed. The standard value $STO_{st}$ is switched to that corresponding to the internal body part identified, and then the difference Δ between the average value $STO_{ave}$ and the standard value $STO_{st}$ is calculated. In other words, the changing section 74 functions as a location detection section.

Alternatively, a well-known image recognition technique may be used for automatically detecting the anatomical location of the internal body part. For example, cardia that is a junction with a unique shape between the esophagus and the stomach may be detected using pattern recognition. In another example, a dark area in the image is compared with a threshold value to detect the anatomical location because the dark area in the image of esophagus is small before the endoscope passes through the cardia while the dark area in the image of stomach is large when the endoscope enters the stomach. Any methods can be employed as long as the internal body part being observed is recognized or identified. For example, an image of a patient being examined can be captured using CT scan to detect the position of the distal portion 17 of the electronic endoscope 10 in the body cavity. Alternatively, the distal portion 17 may be provided with a pH sensor to identify the internal body part being observed based on pH differences.

In the above embodiment, the preliminary imaging is performed when the blood information acquisition mode is selected. Instead, the preliminary imaging may be performed in response to the command of the operator through the operation unit 48 or the like, regardless of the modes.

Figure 16:
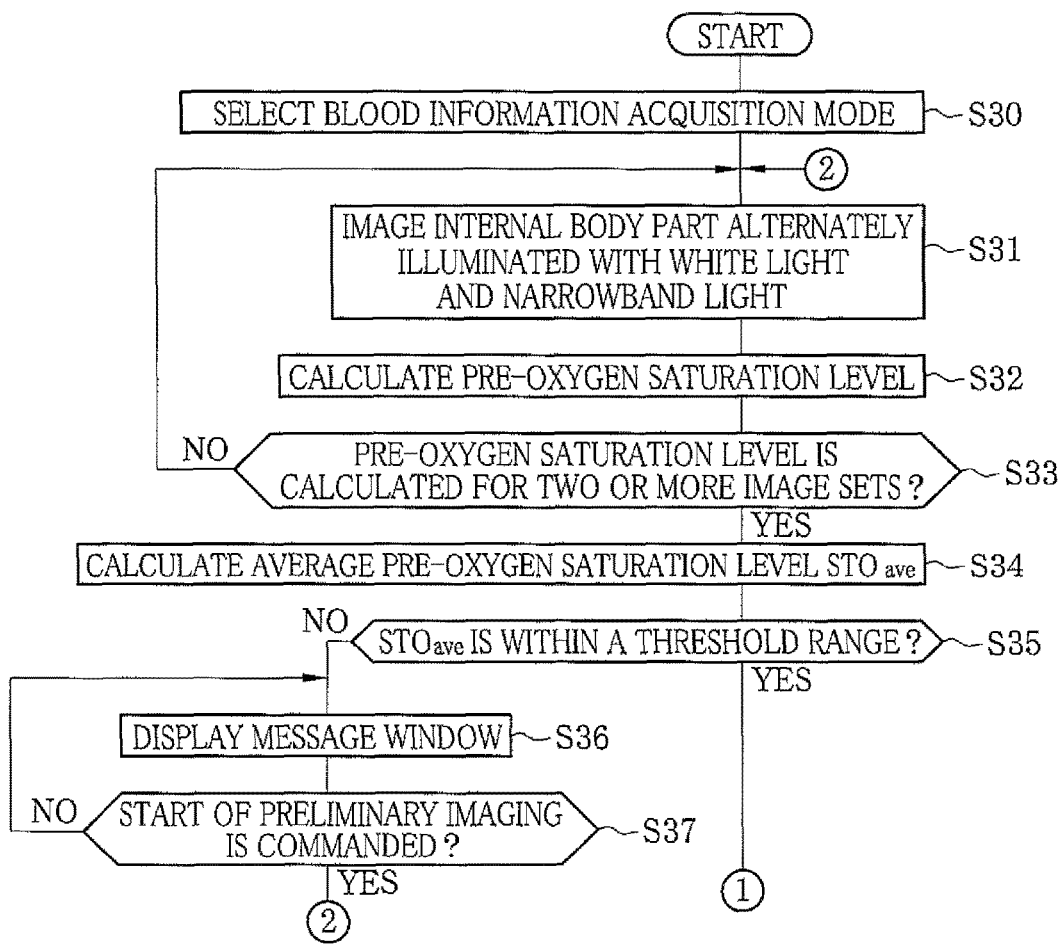
FIG. 16 is a flowchart showing steps for the preliminary imaging performed at the beginning of the blood information acquisition mode.

The preliminary imaging may be started automatically without the command of the operator. In this case, for example, as shown in FIG. 16, the preliminary imaging is automatically started when the blood information acquisition mode is selected (S30) and the average value $STO_{ave}$ of the pre-oxygen saturation levels of the image sets is obtained in a manner similar to the above embodiment (S31, S32, YES in S33, and S34).

Then, the changing section 74 judges whether the average value $STO_{ave}$ is within a predetermined threshold range (permissible range) (S35). In other words, the changing section 74 functions as a judging section for judging whether the internal body part imaged in the preliminary imaging is a normal internal body part. The threshold range may be the oxygen saturation level of 50% or more or 90% or less, for example. When the average value $STO_{ave}$ is within the predetermined threshold range (YES in S35), the changing section 74 judges that the normal internal body part with no lesion is positioned in the whole view field of the electronic endoscope 10. Thereby, the S17 and subsequent steps of the above embodiment are performed.

On the other hand, when the average value $STO_{ave}$ is out of the threshold range (permissible range) (NO in S35), the changing section 74 judges that the internal body part imaged is a lesion. In this case, the message window 80 is displayed on the monitor 18 (S36) in a manner similar to the above embodiment. The message in the message window 80 advises the operator to place the normal internal body part in the whole view field of the electronic endoscope 10. When the operator commands the start of the preliminary imaging (YES in S37), the preliminary imaging is performed again (back to S31). In this way, the step of commanding the start of the preliminary imaging is omitted when the average value $STO_{ave}$ is within the threshold range.

There are various methods for judging whether the internal body part being observed is normal, other than that using the oxygen saturation level described above. For example, a vessel enhanced image (visible image of running blood vessels) of the mucosal surface layer may be analyzed to detect whether the internal body part being observed is normal. The vessel enhanced image of the mucosal surface layer is captured under the illumination of the blue narrowband light (the narrowband light L2 having the center wavelength of 473 nm of the above embodiment, for example). To be more specific, the density or compactness of the blood vessels is obtained from the number of branched blood vessels in the mucosal surface layer. When the density of the blood vessels is high, it is judged that the internal body part being observed includes new blood vessels surrounding the cancer tissue. When the density of the blood vessels is relatively low, it is judged that the internal body part being observed is normal.

In the above embodiment, the average value $STO_{ave}$ is calculated using the oxygen saturation levels of the whole area of the image or image set obtained in the preliminary imaging. On the other hand, an area 20 for calculating the average value $STO_{ave}$ may be limited or specified. For example, the blood information calculation section 70 may judge that an extremely bright area and/or an extremely dark area in the image is unsuitable for calculating the average value $STO_{ave}$, and eliminate or exclude the extremely bright area and/or the extremely dark area. Then the blood information calculation section 70 outputs the information of the pre-oxygen saturation level, corresponding to the remaining area in the image other than the area eliminated, to the changing section 74. To be more specific, when the gradation of the pixel values is expressed by 10 bits, an area with the pixel value out of a range of 30 to 700 is eliminated.

The area 20 for calculating the average value $STO_{ave}$ may be an area in which the ratio r1/g1 between the R pixel value r1 of the first color image P1 and the G pixel value g1 of the first color image P1, being an index of the blood volume, is greater than a threshold value. In other words, the area with the relatively high blood volume may be used as the area 20. As is well known, the cancer tissue causes blood volume deficiency. Therefore, there is a high possibility that the area with the relatively high blood volume is a normal internal body part. On the other hand, when the area has the ratio r1/g1 less than or equal to the threshold value, there is a high possibility that the area is not a normal internal body part, and therefore such area is eliminated from the area 20 for calculating the average value $STO_{ave}$.

The area 20 for calculating the average value $STO_{ave}$ may be an area in which the ratio b2/g1 is greater than a threshold value. The ratio b2/g1 is the ratio between B pixel value b2 of the second color image P2 and the G pixel value g1 of the first color image P1. When the new blood vessels around the caner tissue is imaged, the density or compactness of the blood vessels is relatively high, which makes the ratio b2/g1 relatively small. Namely, when the area has the ratio b2/g1 less than or equal to the threshold value, there is high possibility that the area being imaged has new blood vessels around the cancer tissue. Therefore, such area is eliminated from the area 20 for calculating the average value $STO_{ave}$. Any of the above methods accomplishes fast calculation of the average value $STO_{ave}$ when compared with the calculation of the average value $STO_{ave}$ of the pre-oxygen saturation levels of the whole area of the image set. Thus, the time between after the preliminary imaging and before the main imaging is shortened.

Figure 17:
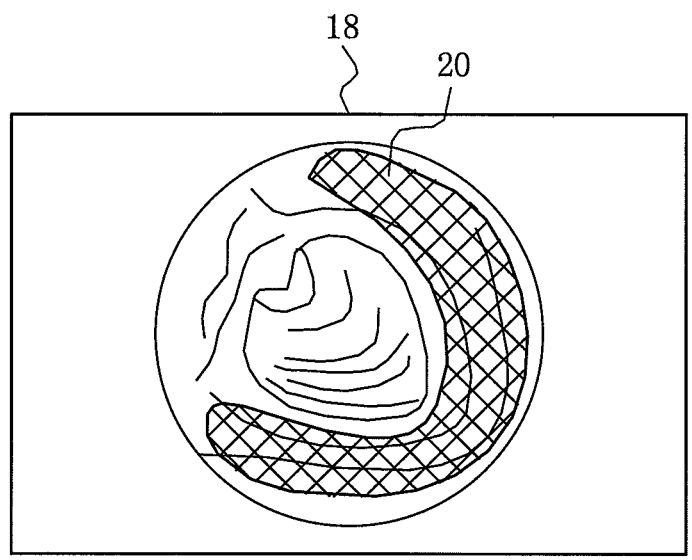
FIG. 17 is an explanatory view of a display of an area used for calculating the oxygen saturation level, by way of example.

As shown in FIG. 17, the area 20 selected for calculating the average value $STO_{ave}$ may be covered with color halftone dot meshing in a distinguishable manner on the oxygen saturation image. Thereby, the area 20 selected is verified by visual observation. Alternatively, the operator may specify the area 20 for calculating the average value $STO_{ave}$. For example, the area 20 may be fixed in a center portion of the image.

The image captured in the preliminary imaging and the information of the pre-oxygen saturation level calculated and the area 20 selected for calculating the average value $STO_{ave}$ may be stored, so that they can be used for verification of the examination, the next examination, or the like.

In the above embodiment, the standard reference data is corrected (when necessary) every time the mode is switched over to the blood information acquisition mode. Alternatively, in addition to the standard reference data, two or more types of corrected reference data may be prepared or made available in advance. Based on the result of the calculation of the difference Δ between the average value $STO_{ave}$ and the standard value $STO_{st}$, the suitable corrected reference data may be selected.

The average value $STO_{ave}$ may be stored and managed on a patient by patient basis or an organ by organ basis of the patient. In this case, without the preliminary imaging, the average value $STO_{ave}$ obtained from the latest examination is retrieved from the storage and used in the above described processes. This saves the trouble of performing the preliminary imaging.

In the above embodiment, the blood volume is calculated in addition to the oxygen saturation level. The present invention is not limited to the above embodiment. The present invention is applicable to a system for calculating only the oxygen saturation level as described in the Japanese Patent Laid-Open Publication No. 06-315477. The present invention is also applicable to a system for obtaining the information of both the oxygen saturation level and the vascular depth as described in U.S. Patent Application Publication No. 2011-0077462 (corresponding to Japanese Patent Laid-Open Publication No. 2011-092690).

In addition to the calculation of the oxygen saturation level, narrowband light with the center wavelengths of, for example, 405 nm, 450 nm, 550 nm, and 780 nm may be applied to the internal body part to obtain the vessel enhanced images of the mucosal surface, middle, and deep layers. The present invention may have a configuration to enable special observation. For example, a fluorescent substance may be ejected into living tissue and excitation light may be applied to the living tissue to observe fluorescence from the living tissue, or intrinsic fluorescence of the living tissue may be observed.

An oxyhemoglobin index calculated by blood volume×oxygen saturation level (%), or a deoxyhemoglobin index calculated by blood volume×(100−oxygen saturation level) (%) may be calculated in the present invention.

In the above embodiment, the first semiconductor laser 55 for the white light and the second semiconductor laser 56 for the narrowband light are used. Alternatively, for example, a white light source such as a xenon lamp, a halogen lamp, or a white LED that emits the white light in a broad wavelength range from blue to red (for example, in a range of 400 nm or more and 800 nm or less) and a wavelength tunable element may be used in combination. The wavelength tunable element selectively passes light in a specific wavelength range of the incident light. The transmissible wavelength range of the wavelength tunable element can be changed.

The wavelength tunable element may be an etalon or a liquid crystal tunable filter, for example. The etalon has two highly reflecting filters. An actuator such as a piezoelectric element is used for changing a space between the two filters so as to control the wavelength band of the light to be transmitted. The liquid crystal tunable filter has a birefringent filter and a nematic liquid crystal cell, sandwiched between polarizing filters. A voltage applied to the liquid crystal cell is changed to control the wavelength band of the transmission light. The wavelength tunable element is provided between the white light source and an incident end of the light guide. Instead, the wavelength tunable element may be provided on an exit side of the light guide. Alternatively, the wavelength tunable element may be provided close to the objective optical system, for example, behind the imaging window or on the imaging surface of the CCD.

Figure 18:
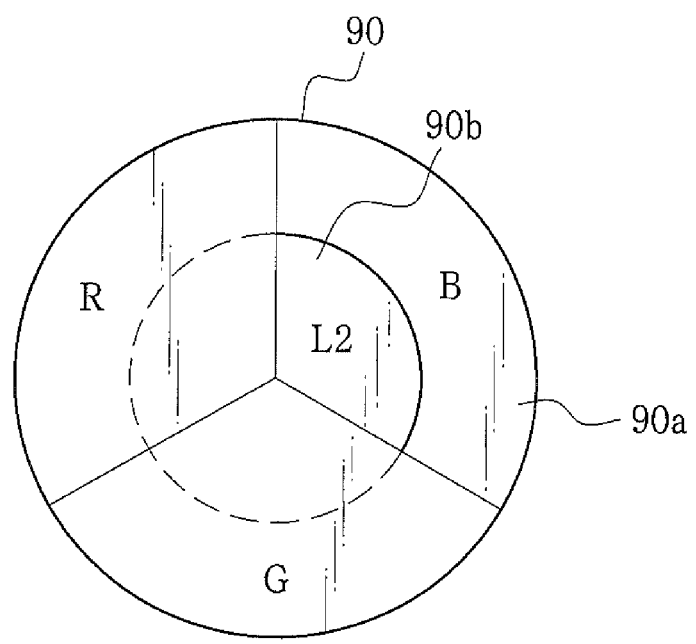
FIG. 18 is a schematic view of a rotary filter.

Alternatively, a monochrome image sensor, a white light source, and a rotary filter may be used. The rotary filter is disposed on a light path of the white light. The rotary filter is provided with two or more interference filters (bandpass filters). For example, a rotary filter 90 shown in FIG. 18 is used. The rotary filter 90 has a dual concentric structure with an outer annular area 90a and an inner circular area 90b. The outer annular area 90a has R, G, and B filter segments. The light in a red wavelength range of the white light passes through the R filter segment. The light in a green wavelength range of the white light passes through the G filter segment. The light in a blue wavelength range of the white light passes through the B filter segment. As for the R and G filter segments, the inner circular area 90b and the outer annular area 90a have the same filter segments. As for the B filter segment, the inner circular area 90b, being a sector or a fan-shaped area, next to the B filter segment of the outer annular area 90a passes light of 470 nm±10 nm (the narrowband light L2).

A shift mechanism (not shown) moves the rotary filter 90 to selectively place one of the outer annular area 90a or the inner circular area 90b on the light path of the white light. In the normal observation mode, the outer annular area 90a is placed on the light path of the white light. Thereby, the R light passed through the R filter segment, the G light passed through the G filter segment, and the B light passed through the B filter segment is applied to the internal body part sequentially. The monochrome image sensor photoelectrically converts reflection light from the internal body part. A full color image for the normal observation is produced from the three color images (R, G, and B). In the blood information acquisition mode, on the other hand, the inner circular area 90b is placed on the light path of the white light. The R light passed through the R filter segment, the G light passed through the G filter segment, and the narrowband light L2 passed through the fan-shaped area of the inner circular area 90b is applied sequentially to the internal body part. In this case, the R light corresponds to the second measurement light, and the G light corresponds to the reference light. A first pixel value is obtained from the imaging with the narrowband light L2. A second pixel value is obtained from the imaging with the R light. The third pixel value is obtained from the imaging with the G light. Instead of the dual concentric structure, the rotary filter may have a structure having two or more fan-shaped areas. Alternatively, two or more rotary filters may be used. The rotary filters may be switched by the shift mechanism.

In the above embodiment, the RGB primary color filter is used as the color filter or the rotary filter of the CCD. Alternatively, a complementary color filter of Y (yellow), M (magenta), and C (cyan) may be used.

In the above embodiment, the electronic endoscope is used by way of example. The present invention is not limited to the above embodiment. The present invention is also applicable to other types of endoscopes, for example, a fiberscope with an image guide or an ultrasonic endoscope incorporating an image sensor and an ultrasonic transducer at its tip.

Various changes and modifications are possible in the present invention and may be understood to be within the present invention.

What is claimed is:

1. An endoscope system comprising:
    a light source for applying measurement light to an internal body part of a subject;
    an imaging device for imaging the internal body part illuminated with the measurement light to output a color pixel value of each pixel;
    a memory for storing standard reference data that defines a correlation between the color pixel value and an oxygen saturation level; and
    a processor, the processor configured for:
        calculating a pre-oxygen saturation level of the internal body part based on the standard reference data and a pre-color pixel value obtained from the imaging device during preliminary imaging;
        changing the standard reference data to corrected reference data in accordance with a difference between the pre-oxygen saturation level and a predetermined standard value of the oxygen saturation level; and
        executing the preliminary imaging and main imaging,
    wherein the imaging device images a normal internal body part with no lesion being illuminated with the measurement light in the preliminary imaging, and images an internal body part with a lesion being illuminated with the measurement light in the main imaging, and
    wherein the processor calculates an oxygen saturation level of the internal body part based on the corrected reference data and a color pixel value obtained from the imaging device during the main imaging.

2. The endoscope system of claim 1, wherein the pre-oxygen saturation level is an average of the oxygen saturation levels of a whole or a part of the internal body part.

3. The endoscope system of claim 2, wherein the processor selectively executes a normal observation mode in which the imaging device captures a color image same as an image observed with a naked eye while the internal body part is illuminated with white light, and a blood information acquisition mode for performing the main imaging.

4. The endoscope system of claim 3, wherein the processor executes the preliminary imaging before the main imaging in the blood information acquisition mode.

5. The endoscope system of claim 2, wherein the color pixel value is composed of three primary color pixel values, and the standard reference data is represented by two or more standard oxygen saturation curves with different oxygen saturation levels in a Cartesian coordinates having two types of ratios as coordinate axes, and the each ratio using two out of the three primary color pixel values, and the corrected reference data is composed of two or more corrected oxygen saturation curves that are shifted from the respective standard oxygen saturation curves in accordance with the difference.

6. The endoscope system of claim 5, wherein the three primary color pixel values are blue, green, and red pixel values, and the measurement light is composed of narrowband light and white light, and the light source applies the narrowband light and the white light alternately in each of the preliminary imaging and the main imaging, and the imaging device obtains a first color image during application of the white light and a second color image during application of the narrowband light, and one of the coordinate axes of the Cartesian coordinates is a ratio between a green pixel value and a red pixel value in the first color image and the other coordinate axis is a ratio between the green pixel value in the first color image and a blue pixel value in the second color image, and the processor uses color pixel values of an image set, being the first color image and the second color image obtained successively, and the pre-oxygen saturation level of the normal internal body part is calculated based on the standard oxygen saturation curves on the Cartesian coordinates in the preliminary imaging, and the oxygen saturation level of the internal body part is calculated based on the corrected oxygen saturation curves in the main imaging.

7. The endoscope system of claim 6, wherein the narrowband light is in a wavelength range in which there is a difference in absorption coefficient between oxyhemoglobin and deoxyhemoglobin.

8. The endoscope system of claim 7, wherein the light source applies each of the narrowband light and the white light for two or more times in the preliminary imaging, and the processor calculates the oxygen saturation level per the image set in the preliminary imaging, and the processor obtains an average of the oxygen saturation levels and uses the average as the pre-oxygen saturation level.

9. The endoscope system of claim 7, wherein the process is further configured for calculating a blood volume from the ratio between the green pixel value and the red pixel value in the first color image.

10. The endoscope system of claim 6, wherein the standard value of the oxygen saturation level is determined for each anatomical body part, and the processor selects the standard value corresponding to the anatomical body part.

11. The endoscope system of claim 10, further including an input device for inputting a specific anatomical body part.

12. The endoscope system of claim 10, wherein the processor is further configured for detecting the anatomical body part based on at least one of the first and second color images.

13. The endoscope system of claim 12, wherein the processor detects the anatomical body part based on a blood volume.

14. The endoscope system of claim 6, wherein the processor is further configured for selecting a measurement area used for calculating an average of the pre-oxygen saturation levels of the normal internal body part in the preliminary imaging.

15. The endoscope system of claim 14, wherein the processor determines an area in the first color image, from which an extremely bright and extremely dark areas are excluded, as the measurement area.

16. The endoscope system of claim 14, wherein the processor determines an area, with a blood volume greater than a threshold value, as the measurement area.

17. The endoscope system of claim 14, wherein the processor determines an area, with density of blood vessels less than a threshold value, as the measurement area.

18. The endoscope system of claim 2, further including:
    a display for displaying a message that advises performing the preliminary imaging such that the normal internal body part is placed in a whole view field of the imaging device, and wherein the processor is further configured for judging whether the pre-oxygen saturation level is within a permissible range, and when the pre-oxygen saturation level is out of the permissible range, the message that advises performing the preliminary imaging is displayed again on the display.

19. An endoscope system comprising:
a light source for applying blue narrowband light and white light alternately or applying blue narrowband light, red light, and green light sequentially to an internal body part of a subject;
an imaging device for outputting a blue pixel value of each pixel which imaged the internal body part illuminated with the blue narrowband light, a red pixel value of each pixel which imaged the internal body part illuminated with a red component of the white light or the red light, and a green pixel value of each pixel which imaged the internal body part illuminated with a green component of the white light or the green light;
a memory for storing first standard reference data for defining an oxygen saturation level using a ratio between the green pixel value and the red pixel value and a ratio between the green pixel value and the blue pixel value and second standard reference data for defining a blood volume using a ratio between the green pixel value and the red pixel value; and
a processor, the processor configured for:
  calculating a pre-oxygen saturation level of the internal body part using the first standard reference data and blue, green, and red pixel values obtained by the imaging device in preliminary imaging;
  changing the first standard reference data to first corrected reference data in accordance with a difference between the pre-oxygen saturation level and a predetermined standard value of the oxygen saturation level; and
  executing the preliminary imaging and main imaging,
wherein the imaging device images a normal internal body part with no lesion being illuminated with the measurement light in the preliminary imaging, and images an internal body part with a lesion being illuminated with the measurement light in the main imaging, and wherein the processor calculates an oxygen saturation level and a blood volume of the internal body part based on the first corrected reference data, the second standard reference data and blue, green, and red pixel values obtained from the imaging device during the main imaging.

20. An endoscope system comprising:
a light source for applying measurement light to an internal body part of a subject;
an imaging device for imaging the internal body part illuminated with the measurement light to output a color pixel value of each pixel;
a memory for storing standard reference data that defines a correlation between the color pixel value and an oxygen saturation level;
a processor, the processor configured for:
  calculating a pre-oxygen saturation level of the internal body part with use of the standard reference data and a pre-color pixel value obtained from the imaging device during preliminary imaging;
  changing the standard reference data to corrected reference data when there is a difference between the pre-oxygen saturation level and a predetermined standard value of the oxygen saturation level;
  maintaining the standard reference data when there is no difference between the pre-oxygen saturation level and the predetermined standard value of the oxygen saturation level; and
  executing the preliminary imaging and main imaging,
wherein the imaging device images a normal internal body part with no lesion being illuminated with the measurement light in the preliminary imaging, and images an internal body part with a lesion being illuminated with the measurement light in the main imaging, and
wherein the processor calculates an oxygen saturation level of the internal body part with use of the corrected set reference data and a color pixel value obtained from the imaging device during the main imaging.

21. The endoscope system of claim 20, wherein the blue narrowband light has a wavelength range of 470 nm±10 nm.

* * * * *